United States Patent
Docherty et al.

(10) Patent No.: US 10,460,166 B2
(45) Date of Patent: Oct. 29, 2019

(54) ROBUST SEGMENTATION OF RETINAL PIGMENT EPITHELIUM LAYER

(71) Applicant: CANON KABUSHIKI KAISHA, Tokyo (JP)

(72) Inventors: Andrew Docherty, St Leonards (AU); Ruimin Pan, Macquarie Park (AU)

(73) Assignee: CANON KABUSHIKI KAISHA, Tokyo (JP)

( * ) Notice: Subject to any disclaimer, the term of this patent is extended or adjusted under 35 U.S.C. 154(b) by 1 day.

(21) Appl. No.: 14/932,807

(22) Filed: Nov. 4, 2015

(65) Prior Publication Data

US 2016/0133013 A1 May 12, 2016

(30) Foreign Application Priority Data

Nov. 6, 2014 (AU) ................................ 2014259527

(51) Int. Cl.
| | |
|---|---|
| *A61B 3/00* | (2006.01) |
| *G06K 9/00* | (2006.01) |
| *G06K 9/52* | (2006.01) |
| *G06K 9/46* | (2006.01) |
| *G06T 7/12* | (2017.01) |
| *G06T 7/149* | (2017.01) |
| *A61B 3/10* | (2006.01) |

(52) U.S. Cl.
CPC ......... *G06K 9/0061* (2013.01); *A61B 3/0025* (2013.01); *G06K 9/00617* (2013.01); *G06K 9/4661* (2013.01); *G06K 9/52* (2013.01); *G06T 7/12* (2017.01); *G06T 7/149* (2017.01); *A61B 3/102* (2013.01); *G06K 2009/4666* (2013.01); *G06T 2207/10101* (2013.01); *G06T 2207/30041* (2013.01)

(58) Field of Classification Search
None
See application file for complete search history.

(56) References Cited

U.S. PATENT DOCUMENTS

| | | |
|---|---|---|
| 7,668,342 B2 | 2/2010 | Everett et al. |
| 8,712,505 B2 | 4/2014 | Ishikawa et al. |
| | (Continued) | |

OTHER PUBLICATIONS

C. K. Hitzenberger; B. Baumann; E. Gotzinger; M. Pircher. Segmentation and quantification of retinal lesions in age-related macular degeneration using polarization-sensitive optical coherence tomography; Journal of Biomedical optics Feb. 2010, 6, pp. 1-20.

(Continued)

*Primary Examiner* — Vikkram Bali
(74) *Attorney, Agent, or Firm* — Canon U.S.A., Inc. IP Division

(57) ABSTRACT

A method determining a retinal pigment epithelium identifies a plurality of regions using captured image data of the eye and fits a curve into at least some of the regions. A curve score is determined associated with the fitted curve using at least a distance between the fitted curve and at least some of the regions in which a contribution of the regions to the curve score is biased towards (asymmetric) regions below the fitted curve. These steps are repeated whereupon one of the fitted curves is selected, using the corresponding associated curve score, for classifying some of the regions as forming at least a part of a retinal pigment epithelium.

23 Claims, 27 Drawing Sheets

(56) References Cited

U.S. PATENT DOCUMENTS

| | | | |
|---|---|---|---|
| 2007/0081707 A1* | 4/2007 | Sirohey | G06F 19/3431 |
| | | | 382/128 |
| 2009/0268159 A1 | 10/2009 | Xu et al. | |
| 2012/0127427 A1 | 5/2012 | Guo et al. | |
| 2012/0194783 A1 | 8/2012 | Wei et al. | |
| 2012/0274898 A1* | 11/2012 | Sadda | A61B 3/102 |
| | | | 351/206 |
| 2012/0308108 A1* | 12/2012 | Everett | G06T 19/00 |
| | | | 382/131 |
| 2013/0265543 A1 | 10/2013 | Iwase et al. | |
| 2015/0201829 A1* | 7/2015 | Yang | G01N 21/4795 |
| | | | 382/131 |
| 2016/0157710 A1* | 6/2016 | Tomatsu | A61B 3/0025 |
| | | | 351/206 |

OTHER PUBLICATIONS

Torr, P.H.S.; Zisserman, A.. MLESAC: A new robust estimator with application to estimating image geometry; Computer Vision and Image Understanding 2000, 78, pp. 138-156.
Hiroshi Ishikawa; Daniel Stein; Gadi Wollstein; Siobahn Beaton; Joel Schuman; James Fujimoto. Macular segmentation with optical coherence tomography. Investigative Ophthalmology & Visual Science , Jun. 2005, 46, pp. 2012-2017.

* cited by examiner

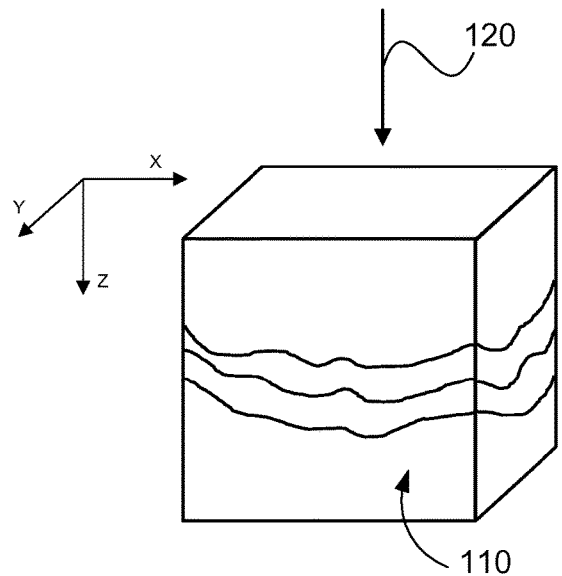
Fig. 1A
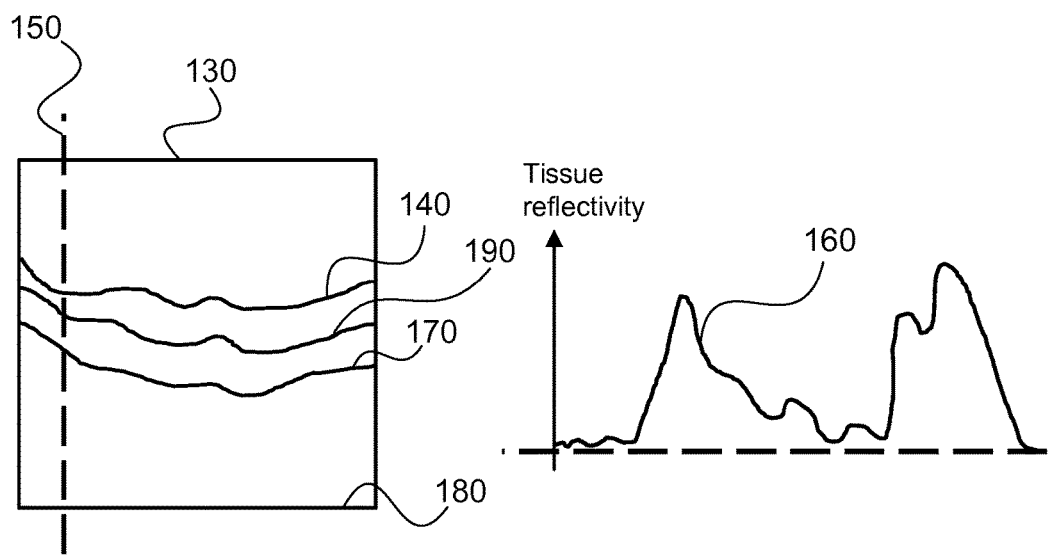
Fig. 1B  Fig. 1C

ROBUST SEGMENTATION OF RETINAL PIGMENT EPITHELIUM LAYER

REFERENCE TO RELATED PATENT APPLICATION(S)

This application claims the benefit under 35 U.S.C. § 119 of the filing date of Australian Patent Application No. 2014259527, filed Nov. 6, 2014, hereby incorporated by reference in its entirety as if fully set forth herein.

TECHNICAL FIELD

The current invention generally relates to methods for optical imaging of biological samples and for processing such images. In particular, disclosed is a method for producing a robust segmentation of a tissue layer to provide diagnostic information.

BACKGROUND

Measurement of the shape and thickness of biological tissue layers can provide useful diagnostic information in many applications. For example, an abnormally thick epicardial adipose tissue layer may be predictive of significant coronary artery disease, and a noticeable thickening of breast tissue can be caused by inflammatory cancer.

In ophthalmology, retinal thickness can be abnormally large in cases of retinal edema or traction by membranes in the vitreous humour. On the other hand, the retina may appear thin in cases of atrophic degeneration, chorioretinitis, or trauma to the retina. In particular, age related macular-degeneration (AMD) is a condition that results in a loss of vision in the centre of the macular because of damage to the retina. Early signs of AMD such as drusen, being cellular debris accumulating between the retina and the choroid, can be detected using the shape of the surface of the retinal pigment epithelium (RPE) layer. A more advanced form of dry AMD, geographic atrophy (GA), can be detected by measuring the thickness of RPE layer.

Optical coherence tomography (OCT) is a medical imaging technique based on low-coherence interferometry employing near-infrared light. OCT produces 3D images with micrometer resolution from within optical scattering media and is widely used in ophthalmology due to the translucent nature of human eye. In Frequency Domain OCT (FD-OCT), the interferometric signal between reference light and the back-scattered light from a sample point in the eye is collected by a line camera. This collected data contains the spectral information of the backscattered signal. After converting the back-scattered light from wavelength to the frequency domain, a one-dimensional Fourier transform is taken to obtain a 1-D spatial distribution of the object scattering potential (A-scan). Laterally scanning the sample beam over a series of adjacent A-scans creates a 2-D tomogram, called a B-scan. Volumes are acquired by further scanning the sample beam in another direction to collect a series of B-scans that covers the 3-D volume of interest.

As the RPE layer is darkly pigmented, it absorbs OCT light and only a weak signal is reflected back to the OCT instrument. In order to identify the retinal pigment epithelium (RPE) layer from a set of 3-D OCT data, one segmentation technique uses the highly scattering property of the RPE, where the second major peak in reflectivity in an A-scan is identified as the RPE. Some recent segmentation algorithms extract the RPE layer in an OCT B-scan by looking for reflectivity peaks. However, it is well known that the intensity of the back-scattered signal alone is not sufficient to be able to distinguish tissue types.

In recent years, functional extensions of OCT have been shown to provide additional contrast by recording not only reflectivity profiles but also information about flow velocity (Doppler OCT) or polarization properties (Polarization-Sensitive OCT, "PS-OCT") of the tissues. For example, in the human retina, birefringent, polarization-preserving, and depolarizing structures can be distinguished by PS-OCT. In the last few years, segmentation of RPE was demonstrated using PS-OCT based on the depolarizing character of the RPE layer. In one method, the position of the Bruch's membrane is estimated using a fixed distance from the inner limiting membrane (ILM), where the location of the ILM is detected in a reflectivity OCT B-scan. Within a certain tolerance, depolarizing tissues below the estimated Bruch's membrane location are classified as belonging to the choroid, and other depolarizing tissues in the vicinity of the estimated Bruch's membrane are classified as RPE. The RPE thickness is then calculated and an en face map, showing the RPE thickness of all B-scans, can be used to diagnose geographic atrophy (GA). Because of the assumed fixed distance from the ILM to the Bruch's membrane, this method fails in cases when the ILM is deformed or when large errors occur in ILM detection.

Another method uses a simple smooth surface fitted to a plurality of detected RPE tissues as the estimate of the location of the Bruch's membrane. Due to depolarizing tissues that are not RPE floating in the retinal area, the fitted smooth surface tends to deviate from the Bruch's membrane location and provides an inaccurate baseline for RPE thickness calculation. Furthermore, for eyes with drusen, where build-up of fatty protein between the RPE and the choroid creates ripples and folds in the RPE layer, a surface fitted to detected RPE tissues is no longer a good estimate of the Bruch's membrane location. In advanced cases of AMD, larger and more numerous drusen in the RPE as well as large geographic atrophy (GA) become challenging for the above segmentation methods. The detection of drusen and GA often relies on the accurate segmentation of the assumed healthy RPE location, the RPE location when there is no retinal disease; the large deformation caused by large drusen or GA regions creates unwanted artefacts and noise in OCT or PS-OCT images and automatic segmentation of such images often fails to produce good results.

Therefore, a new robust method is needed to estimate the location of a specific tissue layer.

SUMMARY

It is an object of the present invention to substantially overcome, or at least ameliorate, one or more disadvantages of existing arrangements.

According to one aspect of the present disclosure there is provided a method determining a retinal pigment epithelium, the method comprising:

(a) identifying a plurality of regions using captured image data of the eye;

(b) fitting a curve into at least some of the regions;

(c) determining a curve score associated with the fitted curve using at least a distance between the fitted curve and at least some of the regions, wherein a contribution of the regions to the curve score is biased towards regions below the fitted curve;

(d) repeating steps (b) and (c) at least once; and (e) selecting one of the fitted curves, using the corresponding associated curve score, for classifying some of the regions as forming at least a part of a retinal pigment epithelium (RPE).

According to another aspect of the present disclosure there is provided a method determining a retinal pigment epithelium, the method comprising:

identifying a plurality of regions using captured image data of the eye;

fitting a plurality of curves to at least some of the identified regions, each fitted curve defining a first plurality of depolarising regions a predetermined distance above the fitted curve and a second plurality of depolarising regions the predetermined distance below the fitted curve; and selecting one of fitted curves by biasing in favour of the second plurality of depolarising regions, the selected fitted curve being used to classify some of the depolarising regions as forming at least a part of a retinal pigment epithelium (RPE).

According to another aspect of the present disclosure there is provided a method determining a retinal pigment epithelium, the method comprising:

identifying a plurality of depolarising regions using captured image data;

obtaining a disease related arrangement of depolarising regions relative to the retinal pigment epithelium;

identifying a curve running through at least some of the identified depolarising regions based on the obtained disease related arrangement; and classifying some of the depolarising regions as forming at least a part of a retinal pigment epithelium using the identified curve.

According to another aspect of the present disclosure, there is provided a computer-implemented method for determining a retinal pigment epithelium, the method comprising:

receiving captured image data of the eye, the captured image data comprising multiple points, each point being characterised by a degree of polarisation uniformity and an intensity value;

extracting, for each point, a plurality of features based on at least a degree of polarisation uniformity and intensity values associated with a corresponding region containing said point; and determining a likelihood score that a point of the captured image data belongs to the retinal pigment epithelium based on the extracted plurality of features to determine the retinal pigment epithelium in the captured image data.

The captured image data typically comprises at least one B-scan slice of retina, the B-scan slice comprises intensity image data and polarisation data of an area of an eye.

The methods may further use the intensity image data and polarisation data to produce degree of polarisation uniformity (DOPU) data. Desirably the identifying a plurality of regions comprises determining a plurality of connected components of the DOPU data, so that each depolarising region in the DOPU data is described as at least one connected component.

In a specific implementation, the depolarising regions below the curve are weighted higher than the depolarising regions above the curve in determining the curve score.

In another implementation the method further comprises:

selecting depolarising regions within a predetermined distance to the selected curve;

fitting a smooth RPE curve to the selected depolarising regions;

classifying the selected depolarising regions as forming at least one of RPE tissues, choroid tissues, and other depolarising particles.

Desirably a depolarising region is classified as being part of the RPE if the depolarising region substantially falls within the predetermined distance to the fitted RPE curve. A depolarising region can be classified as choroid if the depolarising region is below the fitted RPE curve at a distance exceeding the predetermined distance. Alternatively a depolarising region is classified as belonging to other depolarising particles if the depolarising region is above the fitted RPE curve at a distance exceeding the predetermined distance. Depolarising regions may be classified using corresponding shape descriptors.

In another implementation the disease related arrangement is modelled using representative image data of an area of an eye having a particular disease based on distribution of depolarising tissues in the representative image data and strength of optical attenuation and scattering in the depolarising tissues.

Other aspects, including computer program code, systems for implementation, and the like, are also disclosed.

BRIEF DESCRIPTION OF THE DRAWINGS

At least one embodiment of the invention will now be described with reference to the following drawings, in which:

FIGS. 1A to 1C show an example of three-dimensional OCT or PS-OCT data of an eye;

DETAILED DESCRIPTION INCLUDING BEST MODE

Context

Figure 2:
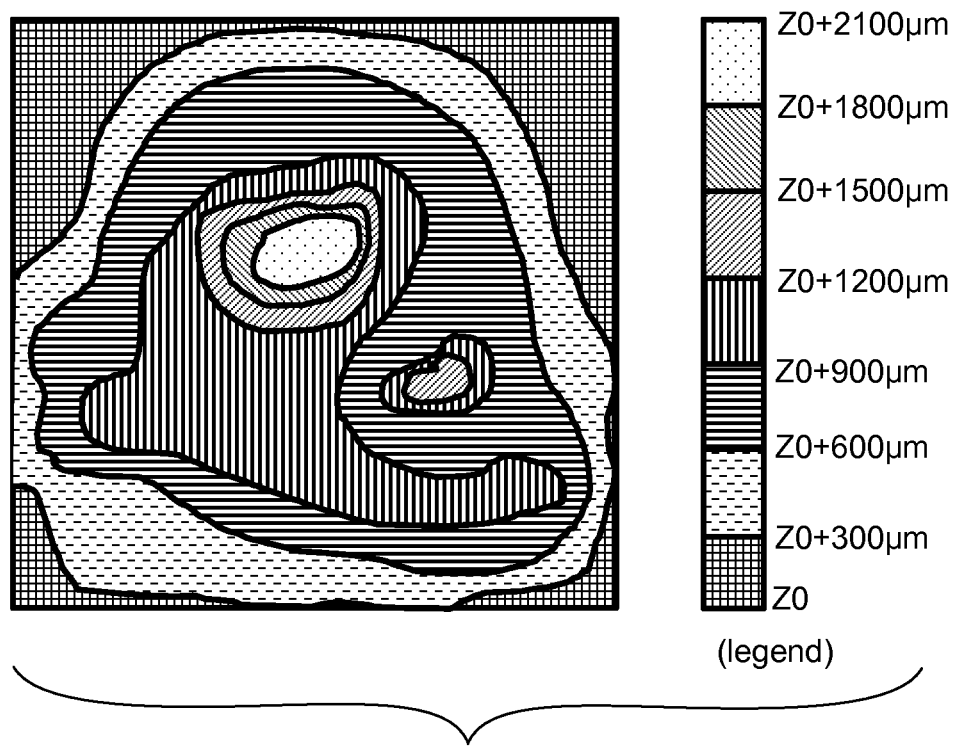
FIG. 2 is a contour plot of the 3D data described in FIGS. 1A to 1C.

FIGS. 1A to 1C show an example of 3D reflectivity data of a tissue sample (e.g. the eye) acquired by an OCT imaging system (not illustrated). In FIG. 1A, 3D OCT data 110 is obtained from an incident sample beam 120 of the OCT imaging system entering the eye. FIG. 1B shows a 2D B-scan 130 representation of an X-Z plane of the 3D OCT data 110. A dashed line 150 in FIG. 1B represents the direction of an A-scan, and FIG. 1C shows an example of an A-scan signal 160. The curves 140, 170, 190 in the B-scan 130 indicate a few highly reflective layers in the tissue sample, which correspond to peaks in the A-scan signal 160. For example, the curve 140 can be the inner limiting membrane (ILM), the curve 190 can be the photoreceptors above the RPE, and the curve 170 can be the RPE layer.

Later in this description, the coordinate system shown in FIGS. 1A to 1C will be used to explain the physical relationship between tissues layers and signal orientations unless indicated otherwise.

FIG. 2 demonstrates a contour representation of the 3D OCT data 110 of FIG. 1A as viewed in the direction 120. The contour plot in FIG. 2 represents the distance from the ILM to a constant depth $Z_0$. In exemplary implementations, $Z_0$ can be taken to be the lowest Z location 180 in the B-scan 130.

Three-dimensional PS-OCT data have similar spatial structure as the 3D OCT data 110 described above. One major difference, however, between a set of PS-OCT data and standard OCT data is that each set of PS-OCT data includes information on the polarization reflectivity properties of the tissue in addition to the intensity reflectivity properties. For each B-scan, PS-OCT produces two complex images $I_1(x, y)$ and $I_2(x, y)$. These two complex images are then used to calculate the polarization and intensity information in the form of the Stokes vector for each image pixel of the 2D B-scan. The Stokes vector has four components giving the reflected wave intensity I, the horizontal and vertical linear polarization Q, the linear polarization at ±45 degrees U, and the circular polarization state V. The Stokes parameters are calculated from the produced complex images $I_1(x, y)=A_1 \exp(i\phi_1)$ and $I_2(x, y)=A_2 \exp(i\phi_2)$, where $A_1$ and $A_2$ are the magnitude of the signals and $\phi_1$ and $\phi_2$ are the phases, using the equation $$I(x,y)=A_1^2+A_2^2$$

$$Q(x,y)=A_1^2-A_2^2$$

$$U(x,y)=2A_1A_2 \cos(\phi_1-\phi_2)$$

$$V(x,y)=2A_1A_2 \sin(\phi_1-\phi_2) \quad (1)$$

From this Stokes vector, a degree of polarization uniformity (DOPU) value is calculated using the equation $$DOPU(x,y)=\sqrt{Q_m^2+U_m^2+V_m^2}, \quad (2)$$

where $Q_m$, $U_m$ and $V_m$ are averaged Stokes vector data calculated by normalizing Q, U, V by I in the Stokes vector, followed by averaging the respective normalized Stokes values using a sliding window. The degree of polarization uniformity (DOPU) in Equation (2) is an image with the same dimension as $I_1(x, y)$ and $I_2(x, y)$. A typical sliding window size is 8-by-10 pixels. The DOPU values calculated in Equation (2) range from 0 to 1. Due to the polarization scrambling property of the RPE, the pixels in the B-scan with low DOPU value are identified as RPE.

In the case of geographic atrophy (GA), the main challenge in RPE segmentation is the high reflectivity and depolarization character of the choroid underneath the RPE. Due to thinning of the RPE or sometimes missing RPE tissues in part of the retina, the choroid underneath demonstrates reflectivity similar to that of the RPE. In addition, some tissues in the choroid, like the RPE, can also be strongly depolarizing. This means distinguishing RPE from depolarizing tissues in the choroid in PS-OCT data is difficult unless depth information is used.

Overview

Information about the health of retinal pigment epithelium (RPE) cells in the retina is important for the diagnosis and monitoring of progression of eye diseases involving the RPE, such as age-related macular degeneration (AMD), geographic atrophy (GA), and retinitus pigmentosa (RP).

Presently disclosed is a system that is capable of robustly determining regions of RPE in a scanned 3-D volume representing the retinal tissue in the eye of a patient having potential or current eye disease. Firstly, depolarizing regions are identified by an analysis of the polarizing information that is collected from back-scattered light from different tissues in the retina. Once the regions of depolarizing nature are identified, they are classified into RPE, choroidal, and other depolarizing particles based on an estimated location of the 'healthy' RPE in the eye if there were no disease. This 'healthy' RPE location is calculated using an assumption that in healthy patients the RPE is smooth. Furthermore, the 'healthy' RPE location is determined by calculating the most likely location for a smooth curve based on the depolarizing tissue locations found in the patient eye as compared to an empirically derived expected probability density function for RPE tissue and depolarizing tissues in the choroid. The expected probability density function is derived using PS-OCT image data representing the retinal tissue in the eye of patients having potential or current eye disease to model an arrangement of depolarising tissues related to that particular disease and/or pathology, such as geographic atrophy. The expected probability density function is further based on the strength of the optical attenuation and scattering in the depolarising tissues.

Once the depolarizing tissues have been classified, the regions of RPE can be used for direct or indirect diagnosis. For example, the thickness of the RPE cells in the 3-D dataset can be presented as a 2D thickness map and areas of thin or absent RPE can be easily seen by a physician.

Structural Implementation

Figure 20A:
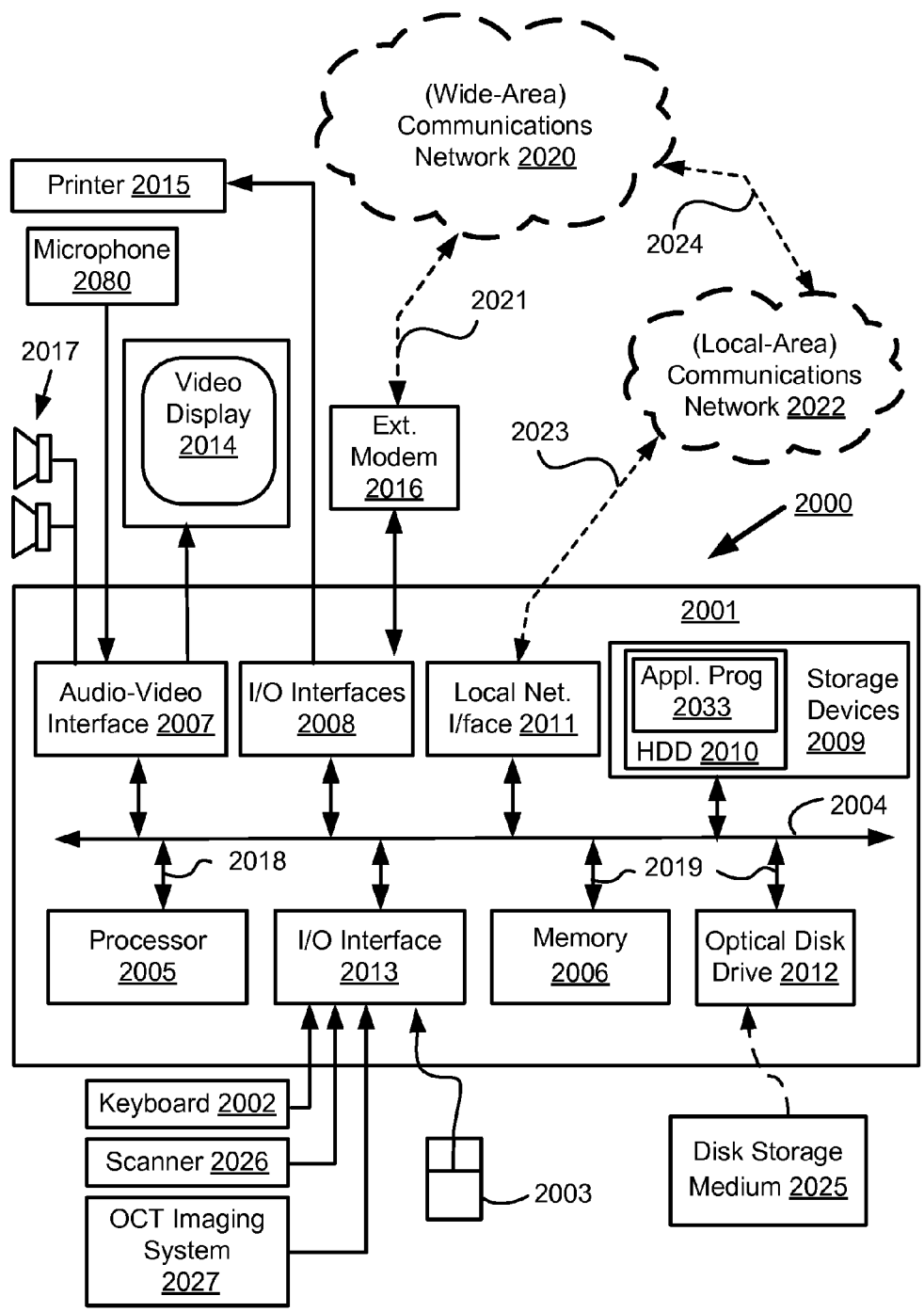
FIGS. 20A and 20B form a schematic block diagram of a general purpose computer system upon which arrangements described can be practiced.
Figure 20B:
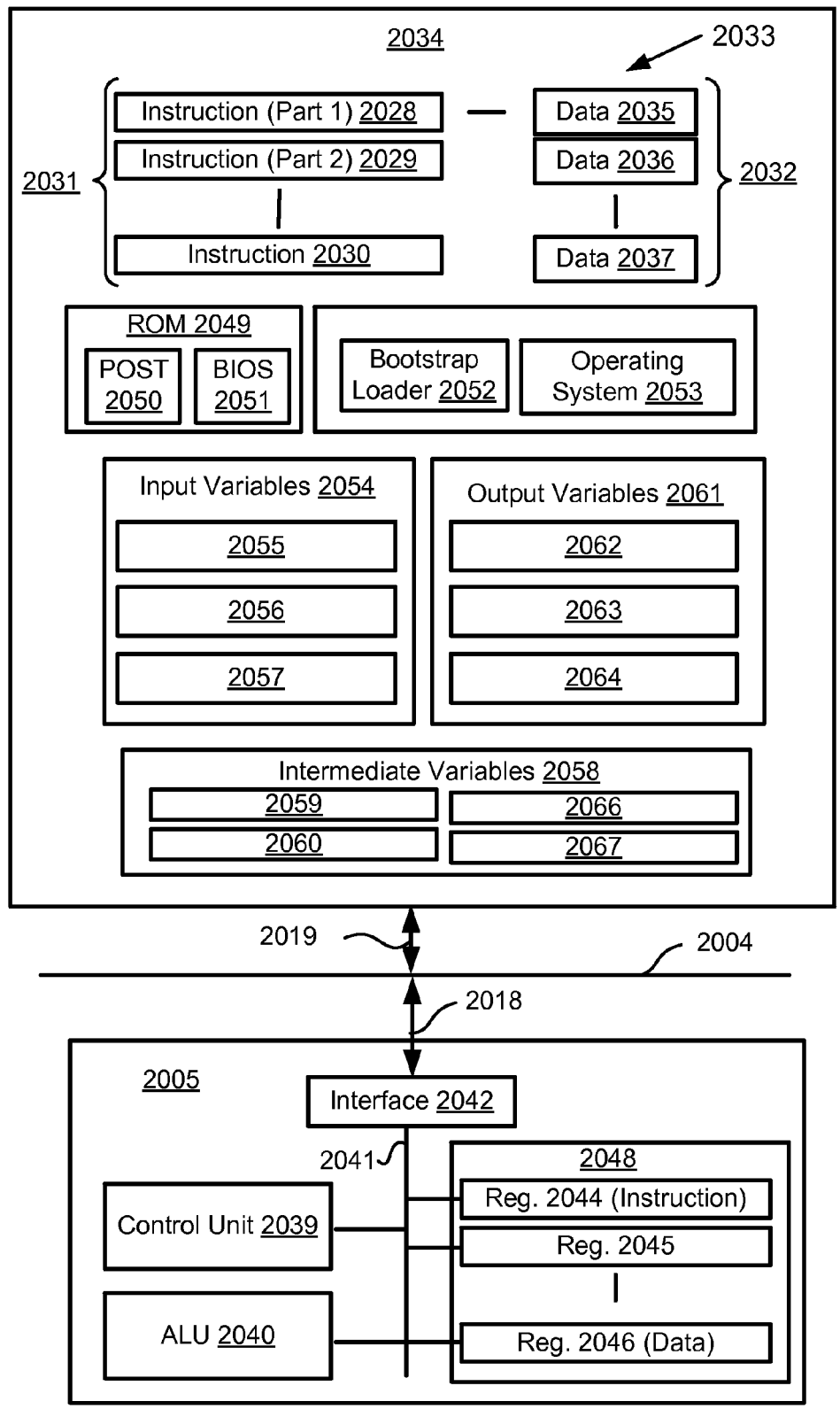

FIGS. 20A and 20B depict a general-purpose computer system 2000, upon which the various arrangements described can be practiced.

As seen in FIG. 20A, the computer system 2000 includes: a computer module 2001; input devices such as a keyboard 2002, a mouse pointer device 2003, a scanner 2026, an OCT imaging system 2027, and a microphone 2080; and output devices including a printer 2015, a display device 2014 and loudspeakers 2017. An external Modulator-Demodulator (Modem) transceiver device 2016 may be used by the computer module 2001 for communicating to and from a communications network 2020 via a connection 2021. The communications network 2020 may be a wide-area network (WAN), such as the Internet, a cellular telecommunications network, or a private WAN. Where the connection 2021 is a telephone line, the modem 2016 may be a traditional "dial-up" modem. Alternatively, where the connection 2021 is a high capacity (e.g., cable) connection, the modem 2016 may be a broadband modem. A wireless modem may also be used for wireless connection to the communications network 2020.

The computer module 2001 typically includes at least one processor unit 2005, and a memory unit 2006. For example, the memory unit 2006 may have semiconductor random access memory (RAM) and semiconductor read only memory (ROM). The computer module 2001 also includes a number of input/output (I/O) interfaces including: an audio-video interface 2007 that couples to the video display 2014, loudspeakers 2017 and microphone 2080; an I/O interface 2013 that couples to the keyboard 2002, mouse 2003, scanner 2026, the OCT imaging system 2027 and optionally a joystick or other human interface device (not illustrated); and an interface 2008 for the external modem 2016 and printer 2015. In some implementations, the modem 2016 may be incorporated within the computer module 2001, for example within the interface 2008. The computer module 2001 also has a local network interface 2011, which permits coupling of the computer system 2000 via a connection 2023 to a local-area communications network 2022, known as a Local Area Network (LAN). As illustrated in FIG. 20A, the local communications network 2022 may also couple to the wide network 2020 via a connection 2024, which would typically include a so-called "firewall" device or device of similar functionality. The local network interface 2011 may comprise an Ethernet circuit card, a Bluetooth™ wireless arrangement or an IEEE 802.11 wireless arrangement; however, numerous other types of interfaces may be practiced for the interface 2011.

The I/O interfaces 2008 and 2013 may afford either or both of serial and parallel connectivity, the former typically being implemented according to the Universal Serial Bus (USB) standards and having corresponding USB connectors (not illustrated). Storage devices 2009 are provided and typically include a hard disk drive (HDD) 2010. Other storage devices such as a floppy disk drive and a magnetic tape drive (not illustrated) may also be used. An optical disk drive 2012 is typically provided to act as a non-volatile source of data. Portable memory devices, such optical disks (e.g., CD-ROM, DVD, Blu ray Disc™), USB-RAM, portable, external hard drives, and floppy disks, for example, may be used as appropriate sources of data to the system 2000.

OCT images, to be processed by the computer system 2000, may be for example sourced directly from the OCT imaging system 2027, or from the either or both of the networks 2020, 2022.

The components 2005 to 2013 of the computer module 2001 typically communicate via an interconnected bus 2004 and in a manner that results in a conventional mode of operation of the computer system 2000 known to those in the relevant art. For example, the processor 2005 is coupled to the system bus 2004 using a connection 2018. Likewise, the memory 2006 and optical disk drive 2012 are coupled to the system bus 2004 by connections 2019. Examples of computers on which the described arrangements can be practised include IBM-PC's and compatibles, Sun Sparcstations, Apple Mac™ or a like computer systems.

The method of image processing, particularly for determining retinal pigment epithelium, may be implemented using the computer system 2000 wherein the processes of FIGS. 5 to 19 and 22 to 25, to be described, may be implemented as one or more software application programs 2033 executable within the computer system 2000. In particular, the steps of the method of retinal pigment epithelium determination are effected by instructions 2031 (see FIG. 20B) in the software 2033 that are carried out within the computer system 2000. The software instructions 2031 may be formed as one or more code modules, each for performing one or more particular tasks. The software may also be divided into two separate parts, in which a first part and the corresponding code modules performs the image processing methods and a second part and the corresponding code modules manage a user interface between the first part and the user.

The software may be stored in a computer readable medium, including the storage devices described below, for example. The software is loaded into the computer system 2000 from the computer readable medium, and then executed by the computer system 2000. A computer readable medium having such software or computer program recorded on the computer readable medium is a computer program product. The use of the computer program product in the computer system 2000 preferably effects an advantageous apparatus for determining retinal pigment epithelium.

The software 2033 is typically stored in the HDD 2010 or the memory 2006. The software is loaded into the computer system 2000 from a computer readable medium, and executed by the computer system 2000. Thus, for example, the software 2033 may be stored on an optically readable disk storage medium (e.g., CD-ROM) 2025 that is read by the optical disk drive 2012. A computer readable medium having such software or computer program recorded on it is a computer program product. The use of the computer program product in the computer system 2000 preferably effects an apparatus for determining retinal pigment epithelium.

In some instances, the application programs 2033 may be supplied to the user encoded on one or more CD-ROMs 2025 and read via the corresponding drive 2012, or alternatively may be read by the user from the networks 2020 or 2022. Still further, the software can also be loaded into the computer system 2000 from other computer readable media. Computer readable storage media refers to any non-transitory tangible storage medium that provides recorded instructions and/or data to the computer system 2000 for execution and/or processing. Examples of such storage media include floppy disks, magnetic tape, CD-ROM, DVD, Blu-ray Disc™, a hard disk drive, a ROM or integrated circuit, USB memory, a magneto-optical disk, or a computer readable card such as a PCMCIA card and the like, whether or not such devices are internal or external of the computer module 2001. Examples of transitory or non-tangible computer readable transmission media that may also participate in the provision of software, application programs, instructions and/or data to the computer module 2001 include radio or infra-red transmission channels as well as a network connection to another computer or networked device, and the Internet or Intranets including e-mail transmissions and information recorded on Websites and the like.

The second part of the application programs 2033 and the corresponding code modules mentioned above may be executed to implement one or more graphical user interfaces (GUIs) to be rendered or otherwise represented upon the display 2014. Through manipulation of typically the keyboard 2002 and the mouse 2003, a user of the computer system 2000 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 2017 and user voice commands input via the microphone 2080.

FIG. 20B is a detailed schematic block diagram of the processor 2005 and a "memory" 2034. The memory 2034 represents a logical aggregation of all the memory modules (including the HDD 2009 and semiconductor memory 2006) that can be accessed by the computer module 2001 in FIG. 20A.

When the computer module 2001 is initially powered up, a power-on self-test (POST) program 2050 executes. The POST program 2050 is typically stored in a ROM 2049 of the semiconductor memory 2006 of FIG. 20A. A hardware device such as the ROM 2049 storing software is sometimes referred to as firmware. The POST program 2050 examines hardware within the computer module 2001 to ensure proper functioning and typically checks the processor 2005, the memory 2034 (2009, 2006), and a basic input-output systems software (BIOS) module 2051, also typically stored in the ROM 2049, for correct operation. Once the POST program 2050 has run successfully, the BIOS 2051 activates the hard disk drive 2010 of FIG. 20A. Activation of the hard disk drive 2010 causes a bootstrap loader program 2052 that is resident on the hard disk drive 2010 to execute via the processor 2005. This loads an operating system 2053 into the RAM memory 2006, upon which the operating system 2053 commences operation. The operating system 2053 is a system level application, executable by the processor 2005, to fulfil various high level functions, including processor management, memory management, device management, storage management, software application interface, and generic user interface.

The operating system 2053 manages the memory 2034 (2009, 2006) to ensure that each process or application running on the computer module 2001 has sufficient memory in which to execute without colliding with memory allocated to another process. Furthermore, the different types of memory available in the system 2000 of FIG. 20A must be used properly so that each process can run effectively. Accordingly, the aggregated memory 2034 is not intended to illustrate how particular segments of memory are allocated (unless otherwise stated), but rather to provide a general view of the memory accessible by the computer system 2000 and how such is used.

As shown in FIG. 20B, the processor 2005 includes a number of functional modules including a control unit 2039, an arithmetic logic unit (ALU) 2040, and a local or internal memory 2048, sometimes called a cache memory. The cache memory 2048 typically includes a number of storage registers 2044-2046 in a register section. One or more internal busses 2041 functionally interconnect these functional modules. The processor 2005 typically also has one or more interfaces 2042 for communicating with external devices via the system bus 2004, using a connection 2018. The memory 2034 is coupled to the bus 2004 using a connection 2019.

The application program 2033 includes a sequence of instructions 2031 that may include conditional branch and loop instructions. The program 2033 may also include data 2032 which is used in execution of the program 2033. The instructions 2031 and the data 2032 are stored in memory locations 2028, 2029, 2030 and 2035, 2036, 2037, respectively. Depending upon the relative size of the instructions 2031 and the memory locations 2028-2030, a particular instruction may be stored in a single memory location as depicted by the instruction shown in the memory location 2030. Alternately, an instruction may be segmented into a number of parts each of which is stored in a separate memory location, as depicted by the instruction segments shown in the memory locations 2028 and 2029.

In general, the processor 2005 is given a set of instructions which are executed therein. The processor 2005 waits for a subsequent input, to which the processor 2005 reacts to by executing another set of instructions. Each input may be provided from one or more of a number of sources, including data generated by one or more of the input devices 2002, 2003, data received from an external source across one of the networks 2020, 2022, data retrieved from one of the storage devices 2006, 2009 or data retrieved from a storage medium 2025 inserted into the corresponding reader 2012, all depicted in FIG. 20A. The execution of a set of the instructions may in some cases result in output of data. Execution may also involve storing data or variables to the memory 2034.

The disclosed processing arrangements use input variables 2054, which are stored in the memory 2034 in corresponding memory locations 2055, 2056, 2057. The processing arrangements produce output variables 2061, which are stored in the memory 2034 in corresponding memory locations 2062, 2063, 2064. Intermediate variables 2058 may be stored in memory locations 2059, 2060, 2066 and 2067.

Referring to the processor 2005 of FIG. 20B, the registers 2044, 2045, 2046, the arithmetic logic unit (ALU) 2040, and the control unit 2039 work together to perform sequences of micro-operations needed to perform "fetch, decode, and execute" cycles for every instruction in the instruction set making up the program 2033. Each fetch, decode, and execute cycle comprises:

(i) a fetch operation, which fetches or reads an instruction 2031 from a memory location 2028, 2029, 2030;

(ii) a decode operation in which the control unit 2039 determines which instruction has been fetched; and (iii) an execute operation in which the control unit 2039 and/or the ALU 2040 execute the instruction.

Thereafter, a further fetch, decode, and execute cycle for the next instruction may be executed. Similarly, a store cycle may be performed by which the control unit 2039 stores or writes a value to a memory location 2032.

Each step or sub-process in the processes of FIGS. 5 to 19 and 22 to 25 is associated with one or more segments of the program 2033 and is performed by the register section 2044, 2045, 2046, the ALU 2040, and the control unit 2039 in the processor 2005 working together to perform the fetch, decode, and execute cycles for every instruction in the instruction set for the noted segments of the program 2033.

The methods of retinal pigment epithelium determination may alternatively be implemented in dedicated hardware such as one or more integrated circuits performing the functions or sub functions of the image processing. Such dedicated hardware may include graphic processors, digital signal processors, or one or more microprocessors and associated memories.

First Implementation

Where reference is made in any one or more of the accompanying drawings to steps and/or features, which have the same reference numerals, those steps and/or features have for the purposes of this description the same function (s) or operation(s), unless the contrary intention appears.

The accurate segmentation of a biological tissue layer often relies on the specific physical attributes of the layer. For example, the inner limiting membrane (ILM) is typically the first tissue layer behind the vitreous body of the eye that strongly reflects incident light. In an OCT B-scan, the ILM stands out as the first bright curve 140 in the Z direction shown in FIG. 1. Similarly, because the RPE layer is highly scattering and depolarizing, the RPE layer can be identified using the reflectivity the RPE layer and the associated low DOPU value, where the DOPU value is calculated using the method described previously.

However, determining the location of the assumed healthy RPE location, i.e. the RPE location when there is no retinal disease, is less straightforward in the tomograms of an eye with GA, where part of the RPE is missing due to the atrophy. The Bruch's membrane sits between the RPE and the choroid and is a reliable base line for estimating the healthy RPE location. In a healthy eye without RPE deformation caused by conditions such as drusen, the healthy RPE and the Bruch's membrane are next to each other. In an eye with GA, even when the RPE is deformed or part of the RPE layer is missing, Bruch's membrane is generally still attached to the choroid. Therefore, the Bruch's membrane location is often a good estimate of the healthy RPE location. In an OCT B-scan of an eye without GA, due to the strong scattering effect of the RPE, the Bruch's membrane layer is normally not visible. By contrast, in an eye with GA, the Bruch's membrane and the choroid underneath are visible. Unfortunately, in an intensity OCT image with pathologies such as GA where Bruch's membrane is visible, practitioners find it difficult to reliably differentiate from the RPE layer above Bruch's membrane and the choroid layer below Bruch's membrane as they all have similar reflectivity.

Figure 3A:
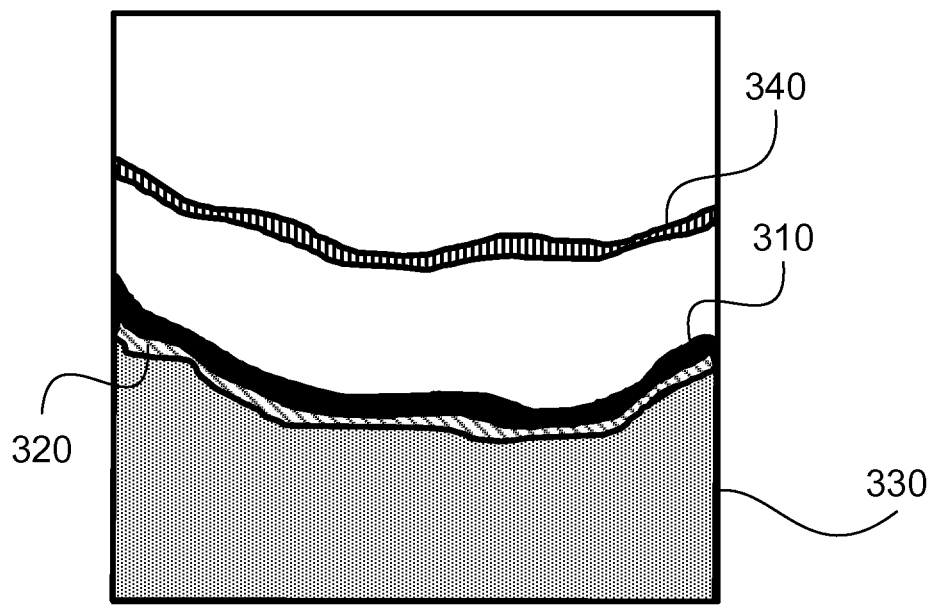
FIG. 3A shows an example of an OCT or PS-OCT B-scan.
Figure 3B:
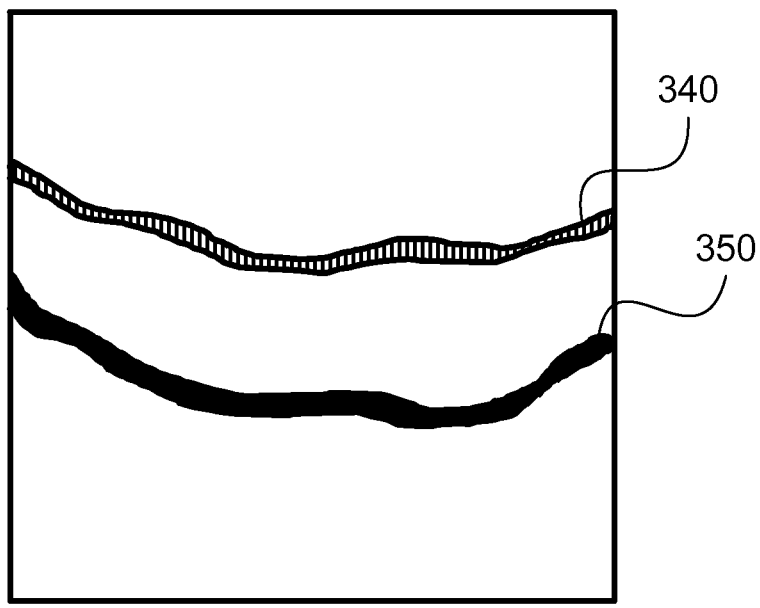
FIG. 3B shows an example of an OCT B-scan with highlighted inner limiting membrane (ILM) and retinal pigment epithelium (RPE)

FIG. 3A shows the ILM 340, the RPE 310, Bruch's membrane 320, and the choroid 330 in the X-Z plane indicated in FIG. 1. In a healthy eye, the RPE is firmly attached to the Bruch's membrane, which is firmly attached to the choroid, as shown in FIG. 3A. In an actual OCT B-scan, because of the strong scattering effect of the RPE, the Bruch's membrane 320 and the choroid 330 are not visible. FIG. 3B illustrates an example OCT B-scan showing the ILM 340 and the RPE 350 as the two brightest layers.

Figure 4:
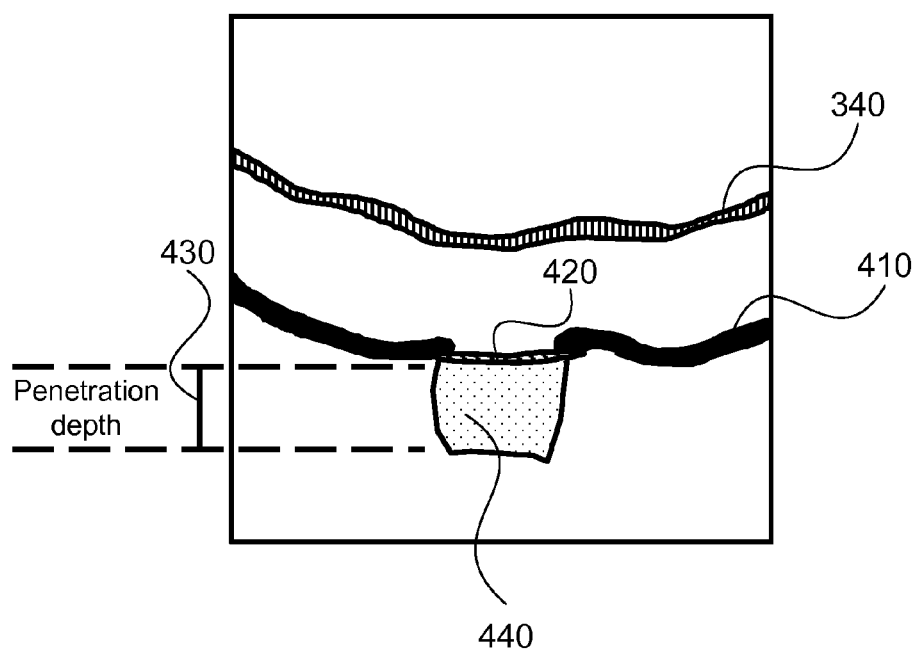
FIG. 4 shows an example of an OCT B-scan where geographic atrophy (GA) is present.

In a diseased eye with GA, the RPE degeneration causes the exposure of the Bruch's membrane and the choroid. An example OCT B-scan in such an eye is illustrated in FIG. 4. In FIG. 4, the middle of the RPE 410 is missing due to the atrophy, exposing the middle of the Bruch's membrane 420 and part of the choroid 440. The choroid 440 shown in FIG. 4 has a thickness that is limited by the absorption and scattering properties of the choroid. This is because the amount of reflected light decreases with the depth of the tissue and the signal to noise ratio drops below a certain threshold at a particular depth beyond which the reflection is considered zero. This depth is referred to as the 'penetration depth', as indicated at 430 in FIG. 4. The penetration depth 430 depends on the strength of the optical attenuation and scattering in the choroid. The inner limiting membrane (ILM) 340 is also shown in FIG. 4 for reference.

The diagnosis of GA using OCT often depends on the identification of the healthy RPE location 410 or Bruch's membrane location 420 as shown in FIG. 4. OCT backscatter intensity as well as the DOPU values calculated from PS-OCT data can be used. Such an approach teaches that when there is a large area of highly scattering or depolarizing tissues below the assumed healthy RPE location, this is because of the exposure of the choroid due to the atrophy. The arrangements presently disclosed use the DOPU image to find a robust estimation of the healthy RPE as distinct from other depolarizing tissues for the diagnosis of GA and other RPE-related disorders.

Figure 5:
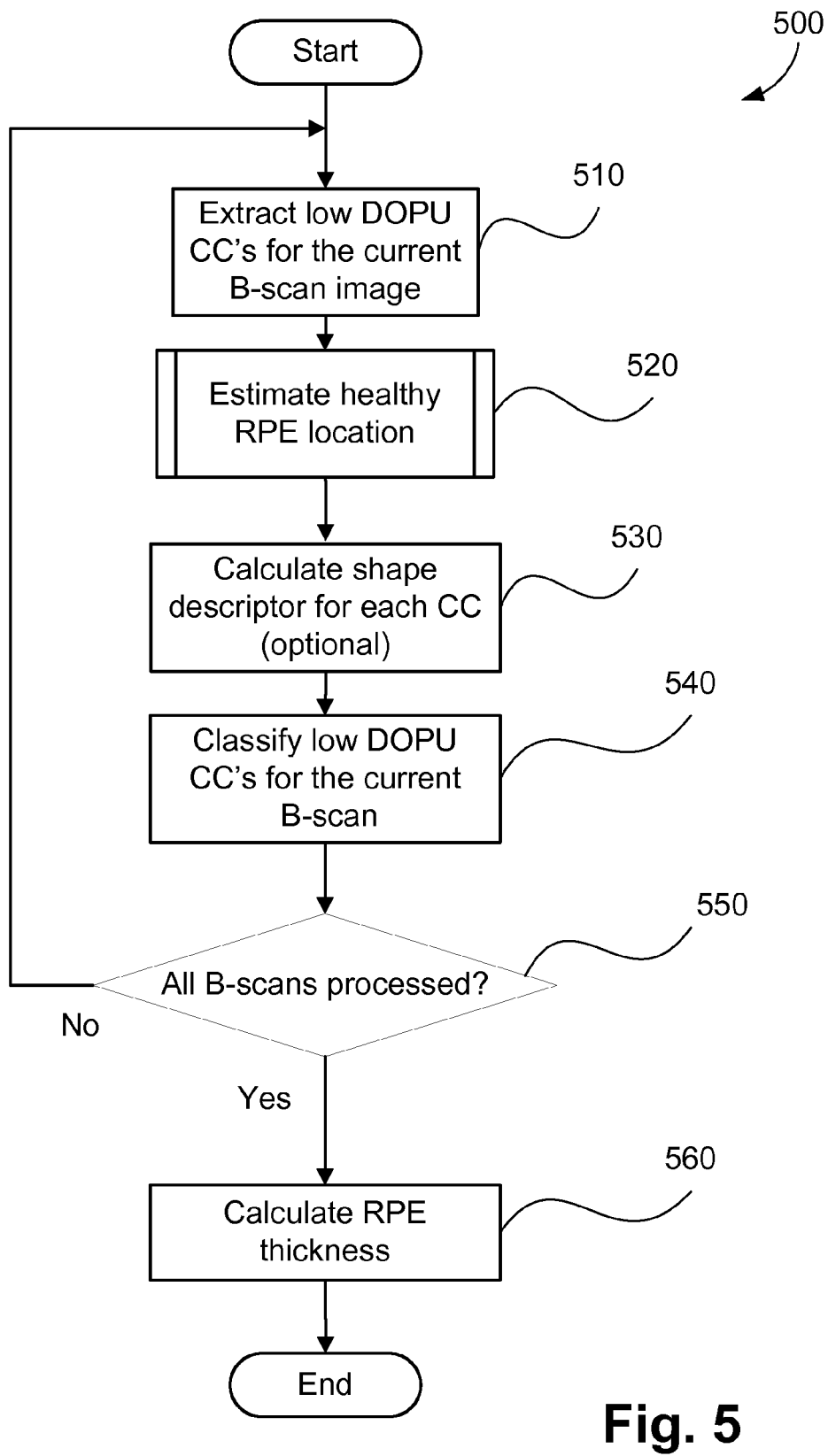
FIG. 5 is a flow diagram showing a method of calculating RPE thickness for the diagnosis of GA.

FIG. 5 depicts the steps of a method 500 for estimation of the RPE thickness from a 3D PS-OCT data set. The method 500 is preferably implemented in software as part of the application 2033 and is executable by the processor 2005 to process an OCT image data set that is typically stored in the HDD 2010 and which may be loaded to the memory 2006 for such processing. The OCT image data set is typically stored or otherwise represented as PS-OCT B-scan data of an eye under examination. For each PS-OCT B-scan, step 510 causes the processor 2005 to extract, from a current B-scan image of the data set, connected components (CC) of pixels with low DOPU values. Step 520 is then executed to cause the processor 2005 to estimate a smooth curve representing the healthy RPE location in the current B-scan using the extracted connected components (CC). An optional step 530 then operates to calculate shape descriptors for each CC in the current B-scan. Step 540 then provides for the processor 2005 to classify each CC as either RPE, disconnected particles above the RPE, or part of the choroid. Specifically, low DOPU CCs are classified as RPE, choroid, or floating depolarising tissues above the RPE using their location relative to an estimated smooth curve as well as information about their shape and the mean DOPU value within the CC. In step 550, the processor 2005 checks if all B-scans in the 3D PS-OCT image set have been processed. If not, the process 500 to step 510 to select an unprocessed next B-scan to thereby repeat steps 510 to 550 to provide a further corresponding classification of the CCs as RPE or other for that B-scan. Where in step 550 the processor 2005 determines that all B-scans in the input data set have been processed, the RPE classified CCs from step 540 are output to calculate the RPE thickness in step 560. More details of the steps in FIG. 5 will be discussed later.

Figure 6:
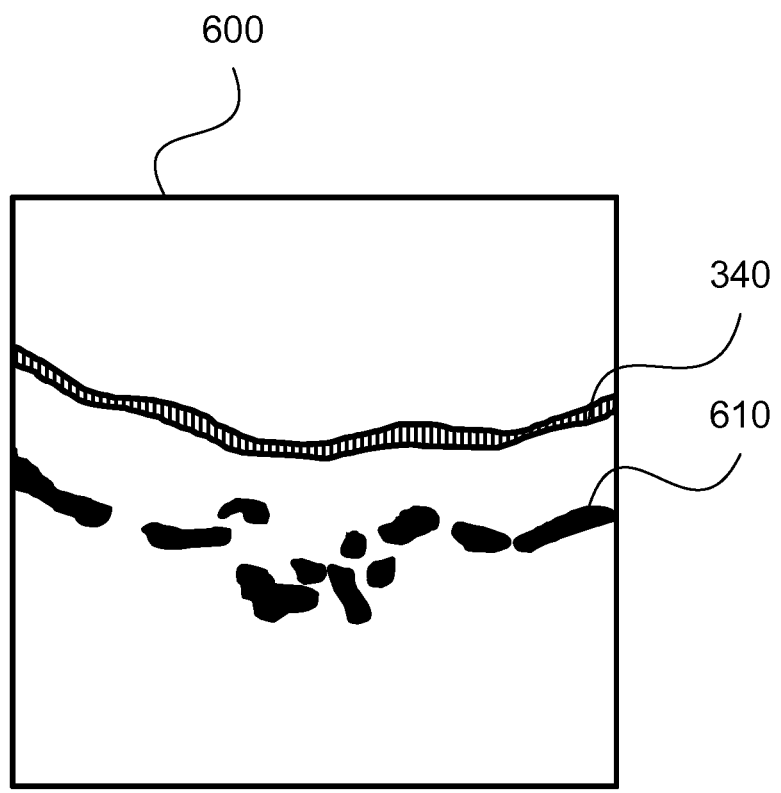
FIG. 6 shows examples of extracted connected components (CC) with low degree of polarization uniformity (DOPU)

FIG. 6 shows an example of extracted low DOPU CC's in a DOPU image 600 obtained using step 510 in a PS-OCT B-scan corresponding to a diseased eye as shown in FIG. 4. The dark regions 610 in FIG. 6 are the extracted low DOPU regions. The ILM 340 is also shown in FIG. 4 for reference. Usually, the extracted low DOPU regions 610 are fragmented and include not only RPE tissues, but also depolarizing tissues in the choroid and particles above the RPE that are also depolarizing.

The low DOPU regions 610 are extracted by finding regions in the image 600 where the DOPU values of the pixels within the region are low enough to determine that this region is depolarizing. The extraction of these low DOPU regions can be achieved using, for example, a method where regions are identified by including neighbouring pixels whose DOPU value falls below a set threshold. This threshold value varies from application to application. In a specific implementation, pixels in the DOPU image with value lower than 0.65 are included in the low DOPU regions. Alternatively, a graph cut segmentation technique could be used to generate a more consistent segmentation by assuming spatial consistency in neighbouring pixels.

Figure 7:
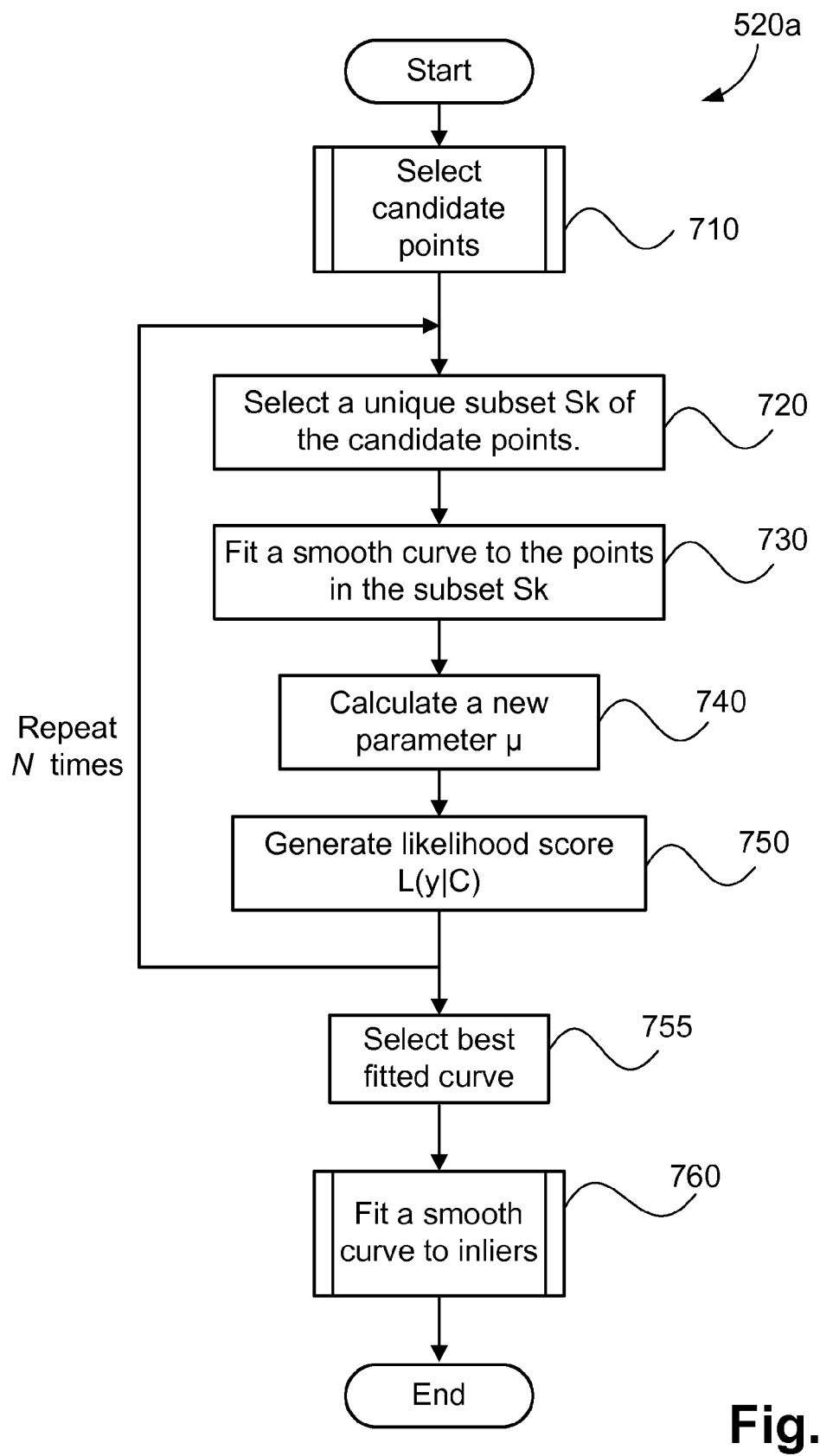
FIG. 7 is a flow diagram showing the details of healthy RPE estimation step in FIG. 5.

Once the low DOPU CC's are extracted, a smooth curve in the B-scan can be estimated to represent the healthy RPE location, i.e., the assumed the RPE location in the same eye without any disease of the RPE. The details of an example of the healthy RPE location estimation performed in step 520 are explained with reference to FIG. 7. As discussed earlier, estimation of the assumed healthy RPE location faces the challenge of unwanted artefacts from depolarizing tissues in the choroid. FIG. 7 lays out the steps of a robust estimation of an exemplary healthy RPE location method 520a where prior knowledge such as the average RPE thickness and the optical attenuation rate in the choroid is taken into consideration. In this robust estimation process, the optical attenuation rate in the choroid guides the determination of the assumed healthy RPE location when there is geographic atrophy (GA).

In FIG. 7, for the exemplary method 520a, step 710 selects a group of candidate points from the low DOPU CCs. Details of the candidate point selection will be discussed with reference to FIG. 9. After the candidate points are selected in step 710, an iterative process repeats steps 720, 730 740 and 750 a predetermined number (N) times, where N is generally greater than 500.

In step 720 the processor 2005 operates to select a small number of points. Thus, for each of the N iterations, a new subset of the candidate point set is chosen. Generally this subset should include just enough points to fit a smooth curve, such as smoothing spline curve. For example, when a smoothing spline is used to model the smooth curve, the number of points generally ranges from 4 to 10. In a specific implementation, 6 points are used.

Figure 8A:
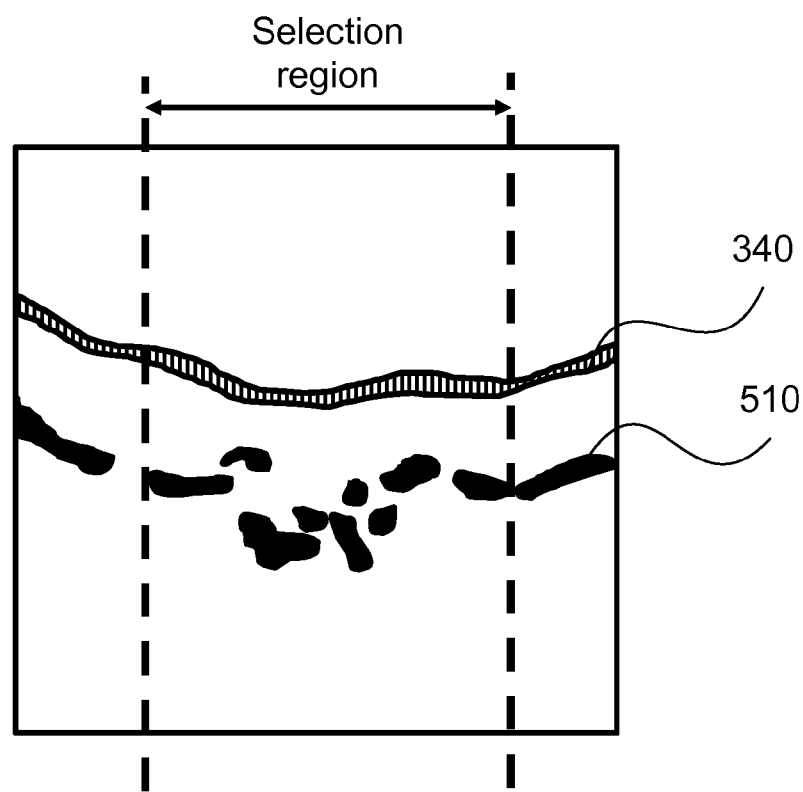
FIG. 8A and FIG. 8B illustrate methods of candidate point selection.
Figure 8B:
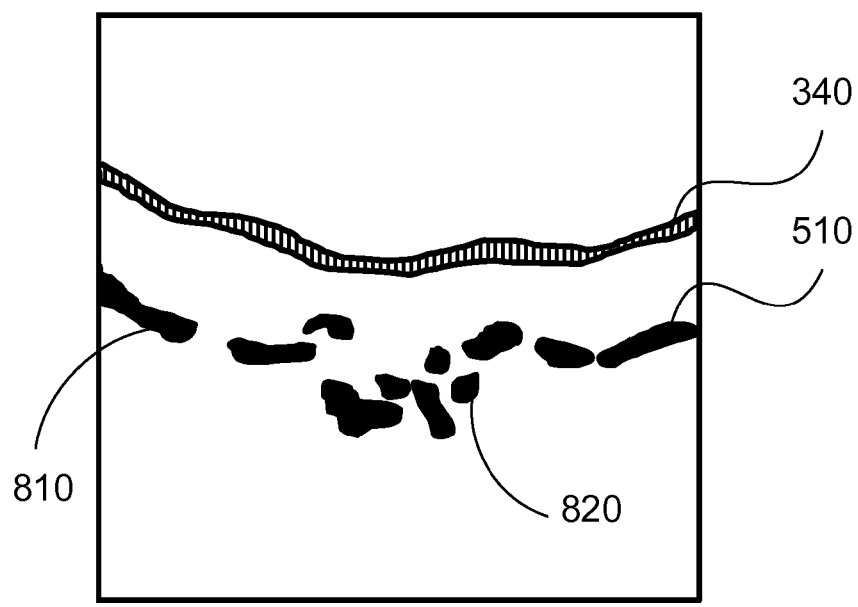

The subset of the candidate points can be selected at random, or based on a certain criteria. In particular, if there is other information that can be used to a-priori estimate the probability that a particular CC is likely to be RPE tissue, then this other information can be used to guide the random selection process to choose these regions with high probability. For example, points can be selected more frequently if they are closer to the centre of the B-scan, as shown in FIG. 8A ("selection region"). Alternatively, locations are selected preferentially based on the shape of the CCs that they belong to, as shown in FIG. 8B (for example, a connected component 810). In FIGS. 8A and 8B, the extracted low DOPU CCs 805 are shown. The ILM 340 is also shown for reference. In FIG. 8A, candidate points in the 'selection region' are selected more frequently than candidate points outside of the 'selection region'. In FIG. 8B, the candidate points from CC 810 are selected more frequently, as the CC 810 is more elongated and has larger area, than are candidate points from CC 820. The area of the CC is calculated as the number of pixels in the CC.

In step 730 the method 520a operates such that the processor 2005 fits a smooth curve to this subset of the candidate points selected in step 720. The smooth curve can be fitted using, for example, a smoothing spline with the coordinates of the subset of candidate points used to fit the spline. This gives the candidate smooth curve $C_k(x)$ for the kth iteration of method 520a shown in FIG. 7.

Step 740 then operates to calculate distribution parameters. More specifically, a mixture parameter $\mu_k$ is calculated by the processor 2005 which determines the appropriate mixture of expected RPE and GA depolarizing tissue probability distribution functions. These probability distribution functions are based on the smooth curve fitted in step 730 and knowledge of the particular tissue layer, such as the average thickness of the RPE. The details of this parameter and the calculation will be explained later.

Step 750 then operates to generate a score based on the expected distribution. More particularly, the processor 2005 generates a 'likelihood score' L(y|C) using the expected RPE and GA probability distribution functions, and the mixture parameter $\mu_k$ calculated in step 740. This likelihood score represents an estimate of the likelihood that the data, represented by the test point locations, has come from the expected conditional probability distribution. The likelihood score may be, for example, a generalized likelihood function or log-likelihood function, and therefore may have values outside the range of 0 to 1. The likelihood score is saved by the processor 2005 to the memory 2006 for comparison to the score of other smooth curves.

Steps 720-750 are repeated N times, where N is a statistically large number, since with a probabilistic approach it is not known deterministically when the best result will be achieved; however, N can be chosen so there is an arbitrarily large probability of successfully finding the best result. This provides for a large number of smooth curves able to be considered for the best estimate of the RPE. Since the steps 720-750 are computationally simple, the processing overhead resulting from a large N is not problematic. In a specific implementation, a "best likelihood score" can be maintained throughout each of the N iterations, permitting the current likelihood score, generated by the current iteration of step 750, to be compared against only the best likelihood score. Where the current score is better (i.e. a higher value), the best likelihood score can be updated with the current score before the next iteration.

On conclusion of the N iterations, step 755 follows where the candidate smooth curve obtained from step 730 with the highest (best) likelihood score is selected to define inliers. A group of inliers is then extracted from all the candidate points selected in step 720. Details of the expected RPE and GA distribution function and the inliers will be explained in later sections.

In step 760, a final smooth curve is fitted to the extracted inliers to represent the healthy RPE location. As an alternative, the smooth curve from step 730 corresponding to the highest (best) likelihood score can be used, but such is based on a limited number of points, and a better smooth curve can be obtained using the larger number of extracted inliers. An inlier is a point which is most likely to be drawn from the expected probability distribution for RPE tissue locations using the optimized mixture parameter $\mu_k$ calculated in step 740 using the final smooth RPE curve. Outliers, on the other hand, are points which are not likely to have been drawn from the expected RPE tissue location distribution. In other words, the expected RPE depolarizing tissue probability distribution function defines an expected RPE location and RPE thickness of the RPE layer. Therefore, tissues located within the expected RPE thickness relative to the final fitted RPE curve are considered to be "inliers", while other tissues are treated as "outliers".

Figure 9:
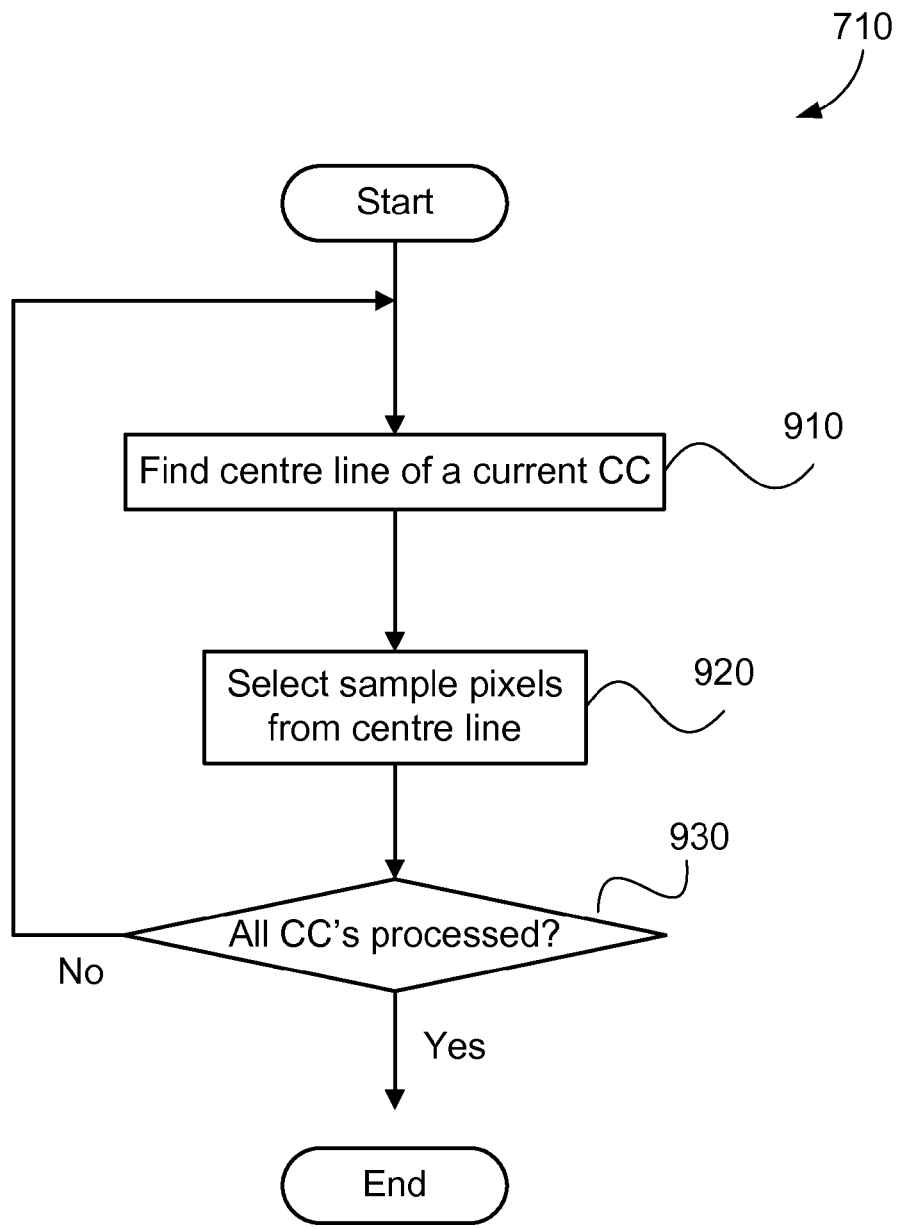
FIG. 9 is a flow diagram explaining the candidate point selection process in FIG. 7.

FIG. 9 shows preferred steps for selecting candidate points as performed in step 710. Step 910 operates to identify a 'centre line' of a current low DOPU connected component (CC) and step 920 samples pixels on the identified 'centre line'. Steps 910 and 920 are repeated for all low DOPU CC's extracted in step 510. In step 930 the processor 2005 checks to determine if all CC's have processed to either exit the method 710 or to return to step 910 to process another CC.

FIG. 11A illustrates the 'centre line' of a low DOPU CC using dashed lines and FIG. 11B shows the sample pixels as black dots. In this example, the 'centre line' 1150 of a CC is the line formed by pixels in the middle of the CC 1140 in the Z direction as indicated in FIG. 11A. In other words, the 'centre line' in FIG. 11A at position $X_0$ 1110 passes through the location $(Z_0+Z_1)/2$, where $Z_0$ 1120 and $Z_1$ 1130 are the two ends of the line segment representing the intersection of the CC 1140 and the vertical line $x=X_0$. In this implementation, the sample pixels (black dots) in FIG. 11B are selected by sampling regularly on the 'centre line' of each CC. For example, 1 in every 10 pixels on the 'centre line' can be used as the sample pixels. Through choosing a representative 'centre line' and sampling the 'centre line' in step 710, the number of low DOPU pixels needed in the computation of steps 720-750 can be greatly reduced.

The following paragraphs discuss the details of the assumed probability distribution function as well as an optimization scheme to calculate the mixture parameter $\mu_k$ in step 740.

The likelihood score is based on the knowledge of the expected probability distribution of depolarizing tissue locations around a 'healthy' RPE location. This expected probability distribution is used to give a score of how likely it is that the data observed could have come from the expected probability distribution given a particular smooth curve. The choice of the expected probability distribution is important to give a robust detection of the correct 'healthy' RPE location.

Figure 12:
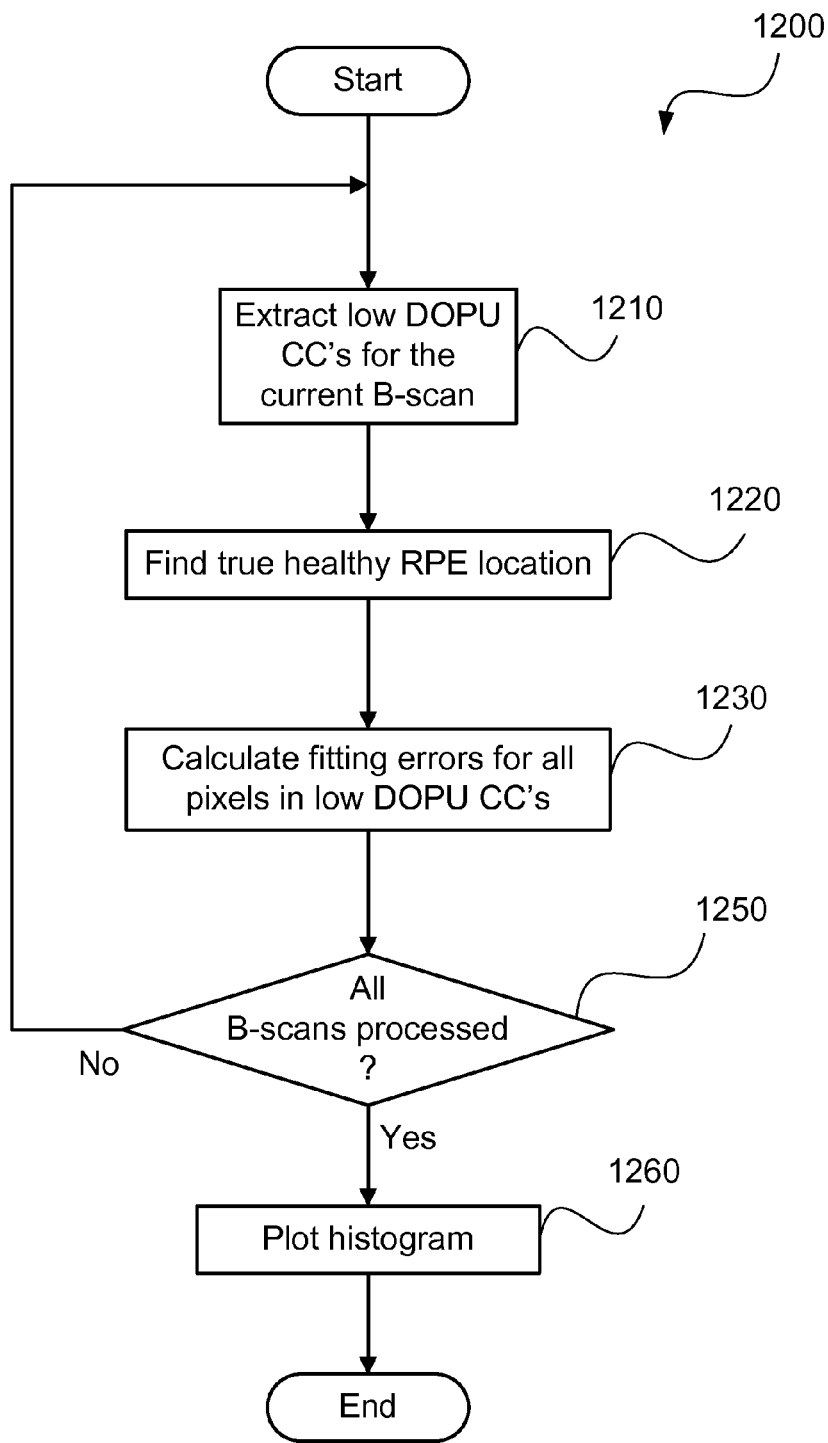
FIG. 12 is a flow diagram describing the histogram generation process.

To determine an appropriate form for this expected probability distribution, a histogram for a small number 3D PS-OCT data sets is plotted. Typically 2-3 data sets are used provided the images are representative of the expected data (PS-OCT image data of an eye with a particular disease) that will be obtained in actual use, although the actual number may be increased. Because the present disclosure is focussed on detecting the assumed 'healthy' RPE location or Bruch's membrane location for eyes with geographic atrophy (GA), 3D PS-OCT data sets with advanced GA are used. A process 1200 for generating this histogram is described in FIG. 12. The process 1200 is typically implemented in software stored on the HDD 2010 and executable by the processor 2005. Execution of the process 1200 is performed pre-emptive of the process 500 as a learning step, for example upon a representative data set in anticipation of processing using real patient data. In FIG. 12, a low DOPU CC extraction step 1210 is used to obtain the low DOPU regions and is the same as the previously described step 510. Step 1220 then executes by which the processor 2005 operates to find the true healthy RPE location (i.e. the "ground truth"), in the form of an estimate of the RPE location, for these PS-OCT data sets using an automatic curve fitting method with manual correction. To save manual effort in step 1220, it is possible to use automatic curve fitting and reject B-scans with less-than-ideal fitted curves. However, as this process need only done once for a particular pathology of interest, the amount of labour is not extreme. Provided the number of B-scans in these PS-OCT data sets is reasonably large, for example, more than 500 slices, the histogram will reveal the shape of the underlying distribution of the depolarizing tissue offset from the true 'healthy' RPE location when a particular eye disorder exists. The identified distribution can further be used as a model for a particular disease, such as geographic atrophy. The histogram therefore is representative of a disease related arrangement (or model) of the depolarising regions above and below, and thereby relative to the RPE.

Once the estimate of the RPE location is set in step 1220, step 1230 executes whereby the processor 2005 calculates the fitting errors for all pixels in the low DOPU CCs of the current B-scan. The fitting error is more specifically described as a depolarizing tissue offset and may be calculated by the processor 2005 using the following formula:

$$E(x) = C(x) - y(x) \quad (3)$$

where $E(x)$ is the depolarizing tissue offset, $C(x)$ is the Z coordinate of the estimated RPE curve at a specific X location, and $y(x)$ is the Z coordinate of a pixel in one of the low DOPU CC's at the same x location. The value $E(x)$ is calculated using all pixels in the low DOPU CC's.

Step 1250 then operates to check if all B-scans in these data sets have been processed. If not, the process 1200 returns to step 1210 to select and process the next B-scan. Once the $E(x)$ values have been calculated for all B-scans, step 1260 operates to plot a histogram of the depolarizing tissue offsets.

Figure 13:
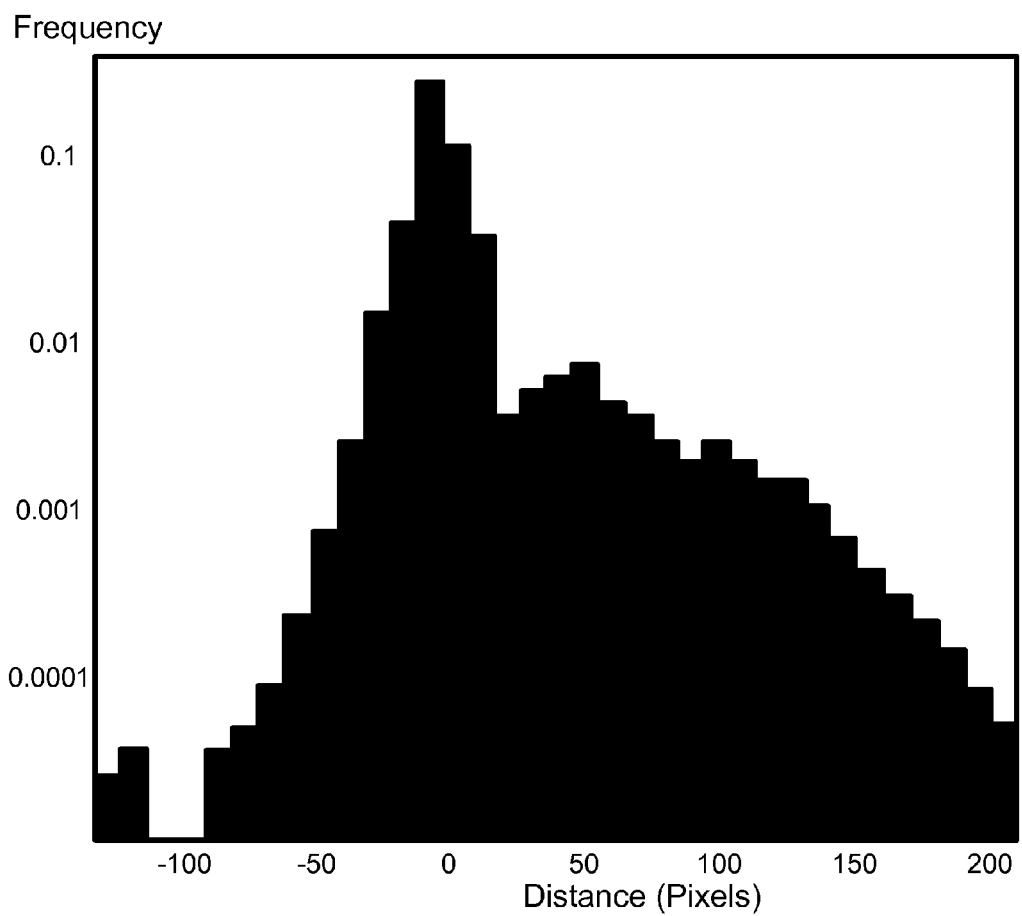
FIG. 13 shows an example of a histogram of the fitting error generating using the process described in FIG. 12.

FIG. 13 shows an example of the histogram generated in step 1260. As such there is one histogram for a data set of images. One histogram may also be formed for a number of data sets. The histogram of FIG. 13 plots frequency of counts of the calculated pixel distances $E(x)$ relative to the estimated RPE curve location at pixel distance 0. Negative values represent distances of CC regions above the estimated healthy RPE curve, and positive values represent distances of CC regions below the estimated healthy RPE curve. Because geographic atrophy (GA) is characterised by extra depolarizing regions underneath the healthy RPE curve in each B-scan, the histogram in FIG. 13 demonstrates asymmetry, such that a contribution of the CC regions to the likelihood score is asymmetrically biased toward regions below the fitted curve of step 730 and thus below the estimated RPE location. This is seen in FIG. 13 where the histogram has a distinct bulge on the positive side of the estimated RPE location (at X=0), and thus below the estimated RPE location. As such depolarising regions in the image data that are below the fitted curve are weighted higher than depolarising regions that are above the curve when determining the curve likelihood score. That is, for PS-OCT B-scans with GA, the distribution of the depolarizing regions or low DOPU regions tends to concentrate in area under the healthy RPE curve with the majority of the low DOPU regions still in a small neighbourhood of the true healthy RPE location, shown as the peak at x=0 in FIG. 13.

Modelling of the distribution in FIG. 13 needs to reflect two important factors. First, a large number of candidate points selected in step 710 should sit in the vicinity of the true healthy RPE location, because the part of RPE not affected by GA is still strongly depolarizing. Second, the candidate points from depolarizing choroid are asymmetrically distributed around the healthy RPE location with almost all of them being under the RPE (with a smaller Z value). In this implementation, a mixture model using the following distributions is proposed:

$$P_{RPE}(y \mid C) = 1 \Big/ \sqrt{2\pi\sigma_{rpe}^2} \; e^{-(C-y)^2 / 2\sigma_{rpe}^2} \quad (4)$$

$$P_{GA}(y \mid C) = \frac{4\sigma_{ga}}{\pi} \frac{(C-y)^2}{[\sigma_{ga}^2 + (C-y)^2]^2} \quad \text{for } y < C \quad (5)$$

$$P(y \mid C) = \mu P_{RPE}(y \mid C) + (1-\mu) P_{GA}(y \mid C) \quad (6)$$

Equation (4) represents a symmetric Gaussian distribution of the depolarizing tissue locations, $y(x)$, associated with the RPE about the 'healthy' RPE location, $C(x)$ found in step

1220. The standard deviation $\sigma_{rpe}$ is proportional to the average RPE thickness. The average RPE thickness can be estimated statistically by averaging across a group of patients. For example, when the B-scan resolution is 3 microns per pixel in the Z direction, $\sigma_{rpe}$ can be set to 5 pixels. In this description, the symmetric Gaussian in Equation (4) will be referred to as the 'RPE probability'. Equation (5) represents an asymmetric function resembling the distribution of candidate points corresponding to the depolarizing tissues in the choroid, where $\sigma_{ga}$ is proportional to the penetration depth of the OCT scanning beam in the choroid as shown in FIG. 4. For example, $\sigma_{ga}$=30 pixels can be used for B-scans where the resolution in Z direction is 3 microns per pixel. In this description, the asymmetric function in Equation (5) will be referred to as 'GA probability'. Equation (6) describes the mixture model where the RPE probability and the GA probability are combined using a weight $\mu$. Although the histogram generated in step 1260 provides a parameterised model for GA ("GA model") as represented by Equation (6), weight $\mu$ usually varies depending on distribution of depolarising tissues of a particular patient. Therefore, to correctly identify an RPE curve and thereby to achieve high quality segmentation, it may be advantageous to determine the weight $\mu_k$ for each iteration in FIG. 7. The determination of the weight $\mu_k$ is outlined below.

Alternatively, if there are large numbers of depolarizing particles that occur at some distance above the RPE region, a third component can be included in the mixture model of Equation (6) that models the probability of depolarizing particles occurring above the RPE. This third component can take the form of a long and constant tail, and the mixing parameter can be taken to be a fixed value or adaptively calculated in a similar way to how $\mu$ is calculated. However, care must be taken to ensure that the function is still asymmetric so that the modelling of GA can be successfully performed.

$$L(y \mid C_k) = \sum_i \log[\mu_k P_{RPE}(y_i \mid C_k) + (1 - \mu_k) P_{GA}(y_i \mid C_k)] \quad (7)$$

Equation (7) gives the log-likelihood function for all test points $y_i$ based on a candidate curve $C_k$ calculated at step 730 and an assumed weight $\mu_k$ at the kth iteration of the N total iterations of the process. The test points $y_i$ in Equation (7) can be the candidate point set as selected in step 710 or they can be a different set of points taken from the connected components, for example all points on the 'centre line' as defined earlier with reference to FIG. 11. The $L(y|C_k)$ value calculated using Equation (7) gives the likelihood score for the curve calculated at step 730 in the kth iteration, as mentioned previously in step 750. This score is used at step 760 to choose the best smooth curve of all the N curves, being the curve with the highest likelihood score.

Figure 14:
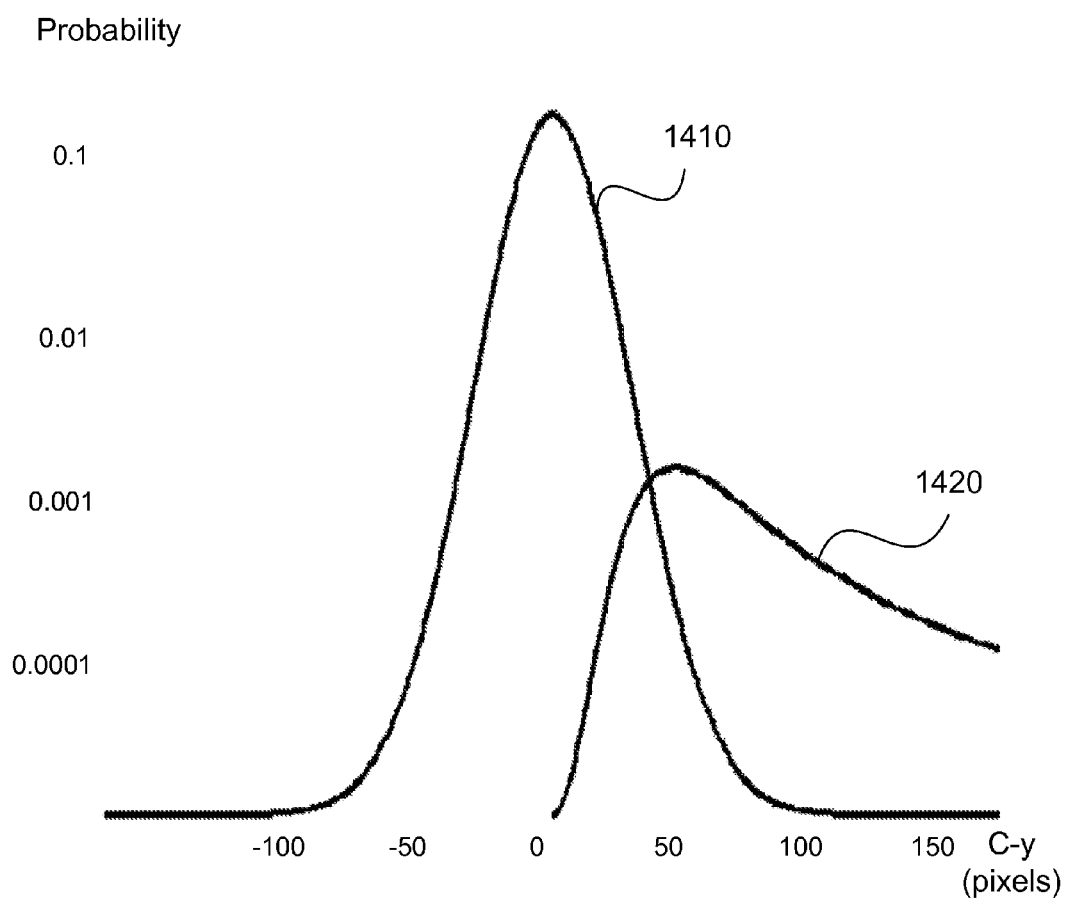
FIG. 14 illustrates the mixture model where two probability distribution functions are combined.

FIG. 14 shows the two distributions described in Equation (4) and (5). FIG. 14 indicates the symmetric RPE probability 1410 and the asymmetric GA probability 1420. The shape of the mixture model in FIG. 14 models GA and is chosen to be similar to the histogram shown in FIG. 13. In B-scans with large GA, where the majority of the RPE is missing, a mixture model with high GA probability value should be used as most of the depolarizing tissues are indeed below the true healthy RPE location. Meanwhile, in B-scans with little atrophy, the mixture model should be dominated by the symmetric Gaussian function 1410 because most of the depolarizing tissues are actually in the RPE layer. In other words, for a B-scan with large GA, a smooth curve is considered a good fit if there are a lot of test points below the curve. Meanwhile, for a B-scan with little or no GA, a smooth curve is considered a good fit if test points are evenly distributed above and below the curve. In Equation (6), the parameter $\mu$ determines if the RPE probability function or the GA probability function dominates. For B-scan slices with large GA, small $\mu$ should be used while for B-scans with small or no GA, large $\mu$ should be used. Because the size of GA in each B-scan is unknown, the value of $\mu$ needs to be estimated iteratively.

In step 740, the best $\mu$ value for the candidate smooth curve calculated in step 730 can be estimated using various optimization methods. For example, maximum likelihood optimization can be used where the log-likelihood of the test points given the candidate smooth curve from 730 is maximized That is, $$\mu_k = \underset{\mu_k}{\operatorname{argmax}} L(y \mid C_k) \quad (8)$$

where $L(y|C_k)$ is the log-likelihood function in Equation (7) and $C_k$ is the candidate smooth curve calculated in step 730 at the kth iteration. This means that the identified weight $\mu_k$ maximises the likelihood value $L(y|C_k)$ for the candidate curve $C_k$ and the distribution of the depolarizing tissue locations $y_i$ fits the identified GA model under the assumption that the candidate curve $C_k$ describes the assumed healthy RPE location. Gradient descent method or expectation maximization (EM) can both be used to find the best $\mu_k$ that maximizes the log-likelihood function $L(y|C_k)$. In general, only 2 or 3 iterations are required to achieve convergence.

Because the optimized $\mu_k$ depends on the candidate smooth curve from step 730, a new optimized $\mu_k$ value is calculated in step 740 and a new likelihood score $L(y|C_k)$ is generated in step 750 for each of the N iterations in FIG. 7. The process in FIG. 7 keeps a record of the highest likelihood score, for example in the memory 2006 as part of the variable 2058. When the iteration finishes in FIG. 7, the fitted smooth curve with the highest likelihood score is identified and inliers are identified in step 760 using this smooth curve to generate a final smooth curve as the estimate of the healthy RPE location.

A preferred implementation of step 760 is now explained with reference to FIG. 10. Suppose the fitted smooth curve with the highest likelihood score is $C_{best}$, the associated likelihood score is $L_{best}$, and the 6 locations used to fit curve $C_{best}$ form a point set $S_{best}$, step 1010 selects a test location t from the candidate locations and forms a temporary point set by combining the location t with the original point set $S_{best}$, if t is not already in $S_{best}$; or alternatively removing t from $S_{best}$ if t is already in $S_{best}$. Similar to the likelihood score calculation in Equation (7), the set of test points used can be a different set of points taken from the connected components, for example all points on the 'centre line' as defined earlier with reference to FIG. 11.

After the temporary point set is formed, a new smooth curve is fitted to the temporary point set in step 1020, and a new likelihood score is generated in step 1030 by the processor 2005 using Equation (7) with the same $\mu_k$ value associated with the original smooth curve $C_{best}$. If the new likelihood score is greater than the highest likelihood score calculated in the iteration steps 720-750, as tested in step 1060, the temporary point set is taken to be a new best set of candidate locations $S_{best}$ in step 1050 and the process 760 goes back to step 1010 to select the next test point if there are more test points to be processed. Otherwise, the process 760 proceeds to step 1070 to check whether all test points have been processed. When not, the process 760 goes back to step 1010 without any change to the best set of candidate locations, $S_{best}$.

After all test points are checked and the original point set S is updated (step 1070=yes), a new smoothing spline is fitted to the updated point set $S_{best}$ in step 1080. The smooth curve fitted in step 1080 will therefore be the final estimate of the healthy RPE location.

Figure 10:
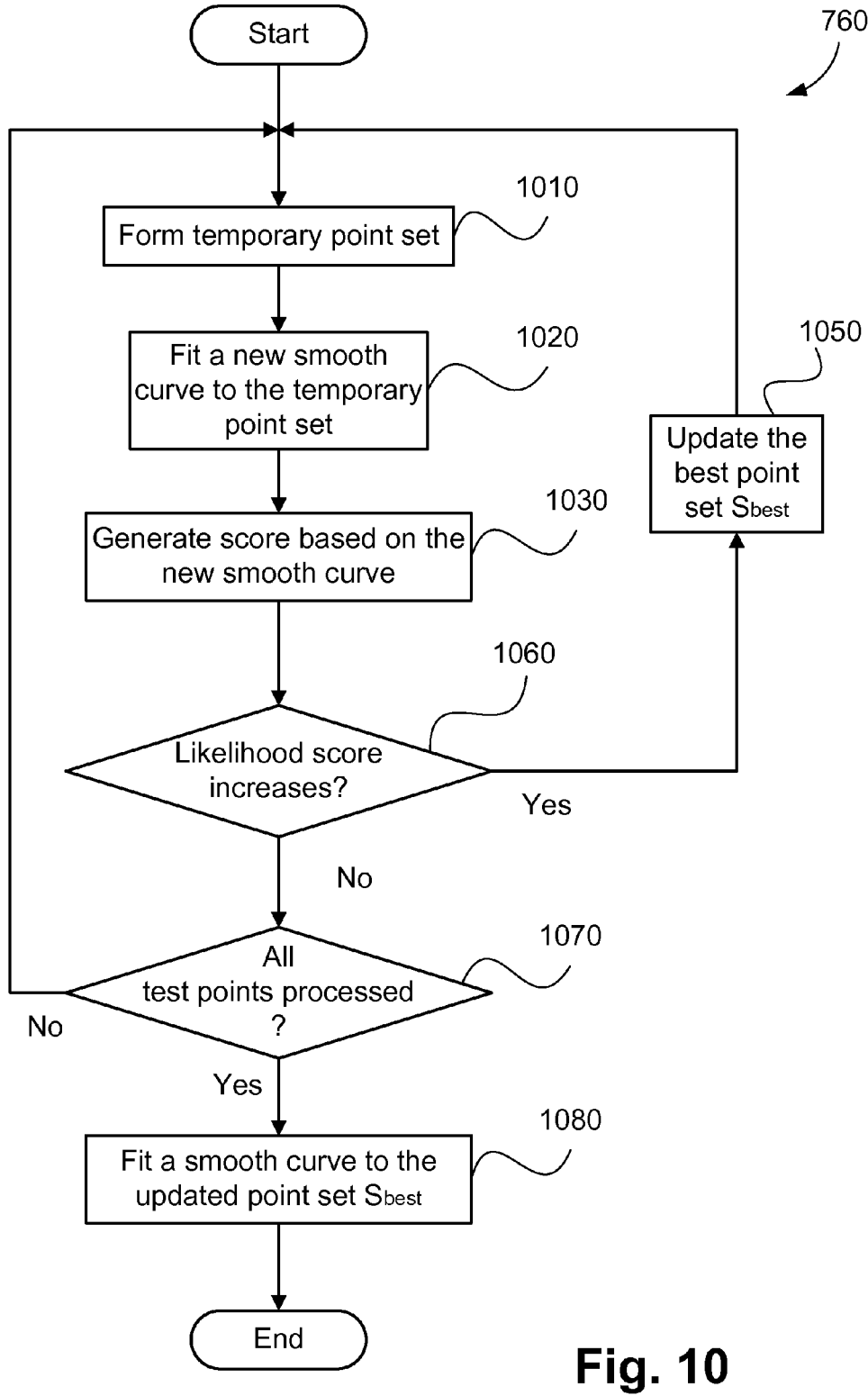
FIG. 10 is a flow diagram showing the final smooth curve fitting step according to FIG. 7.
Figure 11:
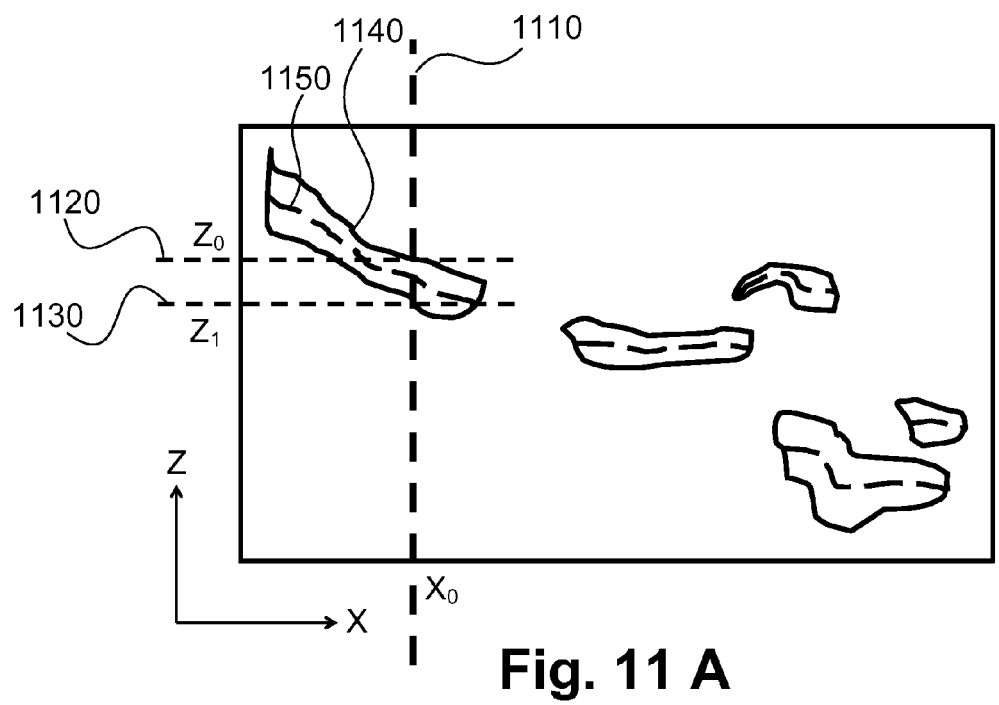
FIGS. 11A and 11B collectively illustrate the candidate point selection process.
Figure 11:
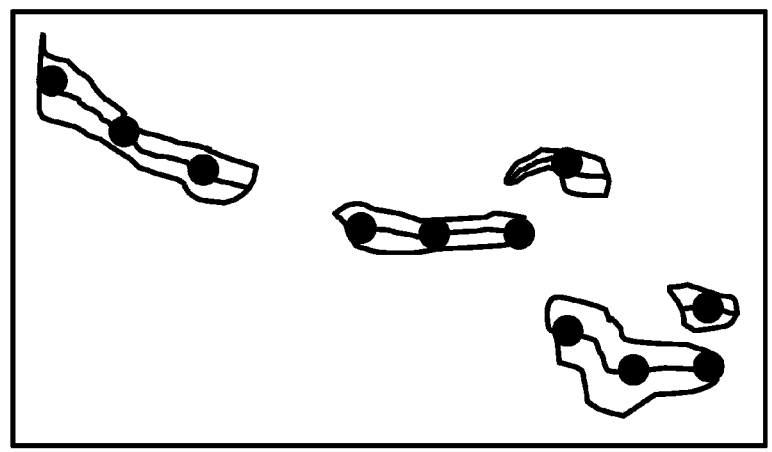
Figure 15:
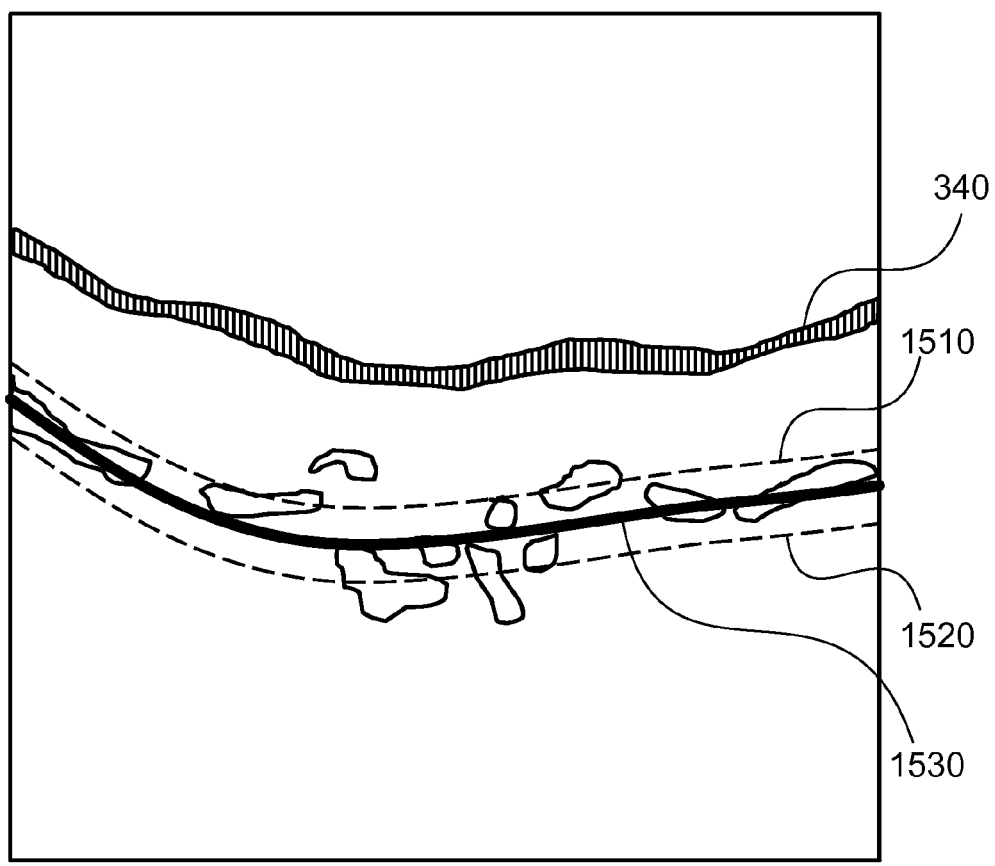
FIG. 15 illustrates the inlier selection process in a B-scan.

In another implementation, the process of FIG. 10 for step 760 is replaced by an inlier selection process where a band centred at the original fitted curve C is used to select inliers. FIG. 15 illustrates this inlier selection criterion. In FIG. 15, candidate points falling between the two dashed lines 1510 and 1520 are considered inliers and any candidate locations outside are considered outliers. The lines 1510 and 1520 are two curves with equal distance from the final smooth curve $C_{best}$, shown as the thick curve 1530 in FIG. 15. For example, the line 1510 can be a shifted version of curve $C_{best}$ 1530 set to be 10 pixels above, and the line 1520 can be a shifted version of curve $C_{best}$ 1530 set to be 10 pixels below. The amount of shift between the lines 1510 and 1530 as well as between lines 1520 and 1530 should be close to the average RPE thickness. In FIG. 15, the ILM 340 and a few low DOPU CC's (unlabelled) are shown as reference. Once the inliers are identified, a new smoothing spline can be fitted to all the inliers to generate a final estimate of the healthy RPE location.

In FIG. 5, once the healthy RPE location is estimated in step 520, an optional step 530 may be used to calculate a shape descriptor for each of the low DOPU CC's identified in step 510. In such an implementation, the eccentricity of each CC is used as the shape descriptor. The eccentricity is a reference to the CC being elongate and generally aligned with the expected RPE. It can be assumed that if a connected component (CC) has an elongated shape, it is more likely to be part of RPE. Eccentricity of a CC can be calculated using image moments or it can be captured using the ratio between the area and the circumference of the CC. Generally, an elongated shape will have a smaller ratio of the area over the circumference. The shape descriptor is used to help exclude small depolarizing particles floating above the RPE (larger Z coordinate values), which tend to appear as small and round CC's. For example, if the ratio between the area and the circumference is less than 3, a CC is considered elongated. If image moments are used, an eccentricity value greater than 0.7 indicates the CC is elongated. Other shape descriptors such as the orientation of each CC can also be calculated. Normally, if a CC is elongated in the direction tangential to the smooth RPE curve, i.e. the CC is aligned with the estimated RPE curve, C(x), it is more likely to be part of RPE. On the other hand, if a CC is elongated in the direction normal to the smooth RPE curve, C(x), it is more likely to be pathological depolarizing tissue.

Figure 16:
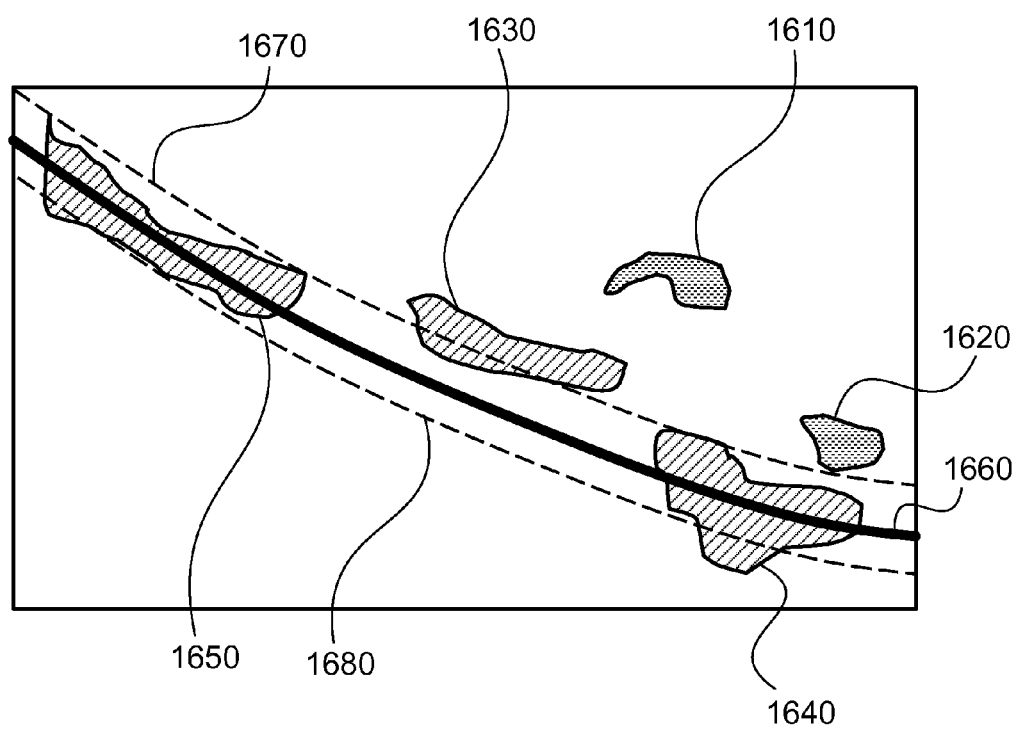
FIG. 16 shows an example of RPE tissue classification in a B-scan.

The classification step 540 uses the estimated healthy RPE location as well as the shape descriptor to classify each low DOPU CC. An example of the classification is shown in FIG. 16. The bold black curve 1660 in FIG. 16 represents the estimated healthy RPE location from step 520, the two dashed curves 1670 and 1680 are the shifted version of the curve 1660 offset 8 pixels in the Z direction from the curve 1660. A depolarising region can be generally classified as being part of the RPE if the depolarising region substantially falls within the predetermined distance to the fitted RPE curve established by the dashed curves 1670 and 1680. Modifications of this are possible. If the majority, for example 50% of a CC falls between the two dashed curves 1670 and 1680, the CC is classified as RPE tissue. If a CC is completely outside, it is considered non-RPE. For a CC with less than 50% of the area between the curves, if a significant percentage, >30% for example, of a CC is between the two curves 1670 and 1680, the shape descriptor is used to determine its classification. For example, CC 1650 and CC 1640 are considered RPE tissues because more than 90 percent of the area of CC 1650 and more than 80 percent of the area of CC 1640 are in between the two curves 1670 and 1680. CC's 1610 and 1620, on the other hand, are not RPE tissue because they are both completely outside the band formed by the lines 1670 and 1680, and may be classified as "other" depolarising particles. For the CC 1630, only a part of the CC 1630 falls in between the two curves 1670 and 1680 and in this example only accounts for about 35% of the area. Because this is less than 50%, the size and the shape descriptor of the CC 1630) is then used. Because CC 1630 is of certain size, for example larger than 40 pixels and the shape descriptor indicates it is an elongated shape with eccentricity aligned with the expected RPE, it is classified as RPE tissue. Where for example a depolarising region (CC) is entirely below the lower dashed curve, and thus the predetermined distance established thereby, such region can be classified as choroid tissue.

Figure 17:
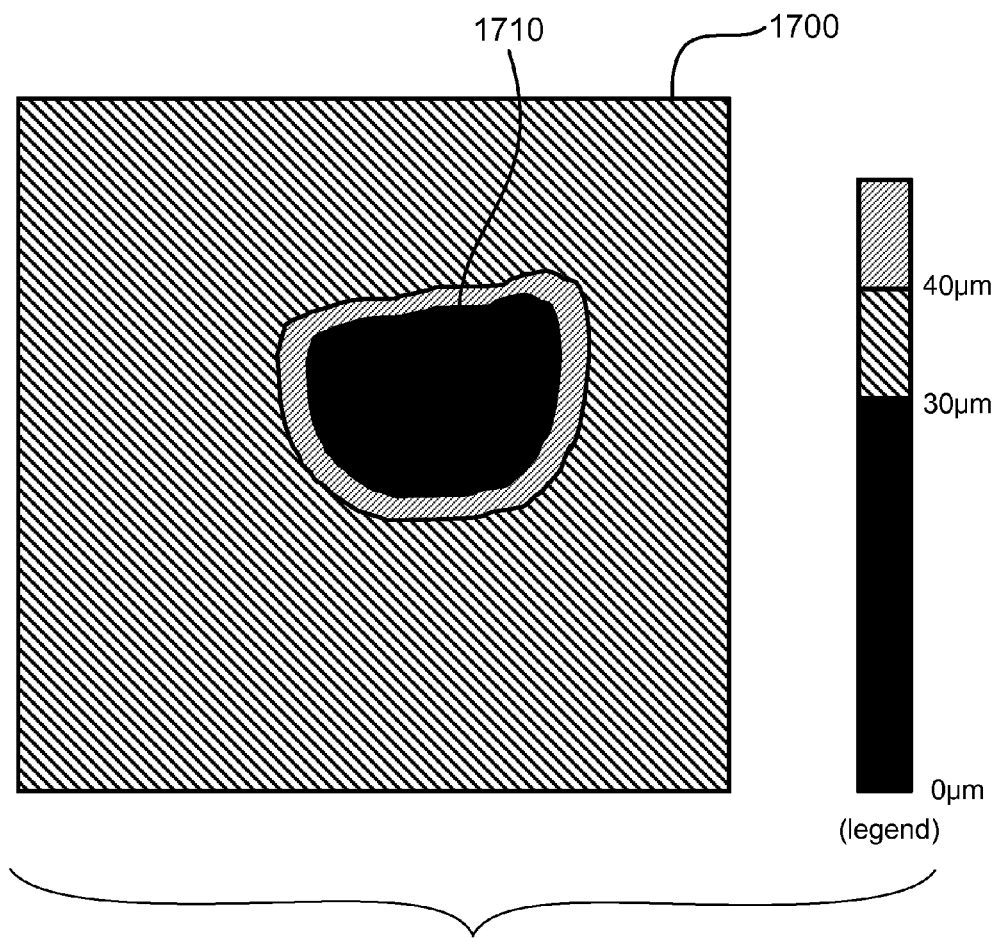
FIG. 17 shows an example of an en face RPE thickness map.

After the iteration in FIG. 5 is finished (the loop of steps 510 to 550), for each B-scan in a PS-OCT data set, some of the pixels have been classified as RPE. When combined, these pixels form a 3D volume representing an RPE tissue layer in the eye. Counting the number of pixels in Z direction for each (X, Y) location in step 560 gives an en face RPE thickness map that reveals degeneration in the RPE tissue including geographic atrophy. FIG. 17 shows an example of an en face RPE thickness map 1700. The dark area 1710 indicates the area of the retina where RPE is diseased or missing. The en face RPE thickness map shown in FIG. 17 can be used to diagnose advanced stage of age-related macular degeneration (AMD) by evaluating the size and number of geographic atrophy (GA) regions.

In addition, the low DOPU regions identified in step 510 of FIG. 5 can be saved as an image in the HDD 2010, where each region is drawn differently according to the classification that it received in step 540 of FIG. 5. For example, FIG. 16 shows a possible output where the RPE regions 1650, 1630 and 1640 are filled with lines and the depolarizing particles 1610 and 1620 are filled with dots indicating the two different classifications that have been determined. Alternatively, each region could be filled with a colour that changed according to the classification. Optionally, this image could be displayed on the display device 2014 as an overlay on top of another raw image data, for example an intensity image showing the strength of the reflectivity of the OCT signal. Medical practitioners can thus use these image as an adjunct in diagnosis. This can further be used to judge the correctness of the classification and modify it if necessary.

Second Implementation

In this implementation, the steps in FIG. 5 are implemented to calculate RPE thickness in a 3D PS-OCT data set, in a manner similar to the first implementation except, the healthy RPE location estimation step 520 is implemented differently.

Figure 18:
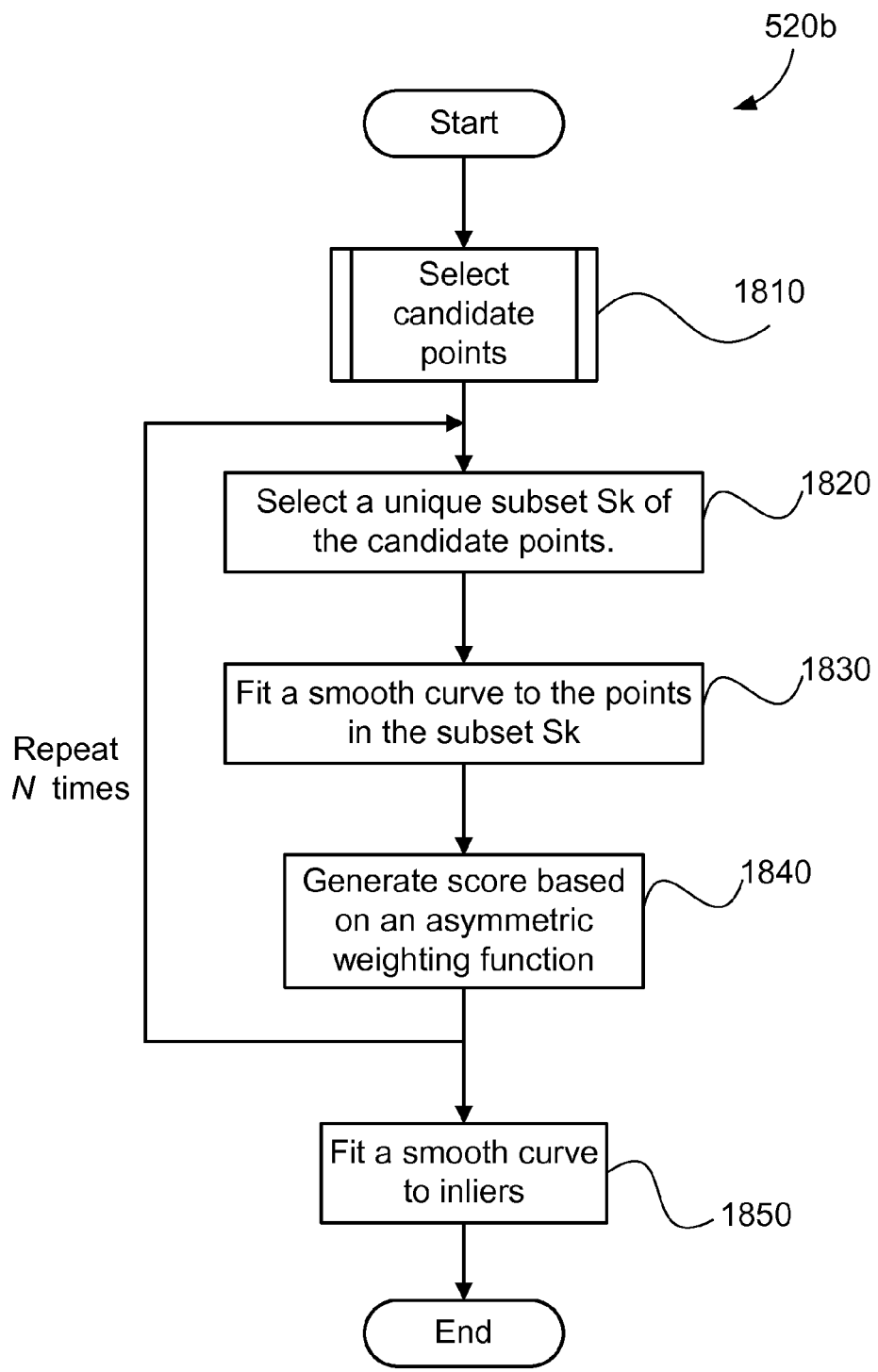
FIG. 18 is a flow diagram explaining the healthy RPE estimation step in FIG. 5 in another implementation.

FIG. 18 shows a preferred process 520b applicable to the second implementation of the process of estimating healthy RPE location 520. First, a candidate point selection process

1810 is used to select the candidate points and which corresponds to that as described above in step 710 of FIG. 7. A unique subset of these candidate points is then chosen in step 1820, as was done in step 720 of FIG. 7. A smooth curve fitting process 1830 is then used to fit a candidate smooth curve to the chosen subset, corresponding to what was done in step 730 of FIG. 7.

To simplify the likelihood score calculation, this second implementation does not use an optimization scheme to find a distribution parameter as was performed in step 740 of FIG. 7. Instead, a simpler scoring function is used based on an assumption that the expected depolarizing tissues will be asymmetrically distributed around the health RPE location. This is because data points from the depolarizing choroid are concentrated in the area under the true healthy RPE location, and there is very little depolarizing tissue located above the true healthy RPE location. In step 1840, an asymmetric scoring function is used to give a score to each fitted curve. As before, steps 1820 to 1840 are repeated N times. In step 1850, the scores of the fitted curves are examined to choose the best smooth curve, which is then used to identify inliers that are used to fit a final smooth curve, in a similar fashion as was done in step 760. The final smooth curve forms the estimate of the RPE location.

Figure 19A:
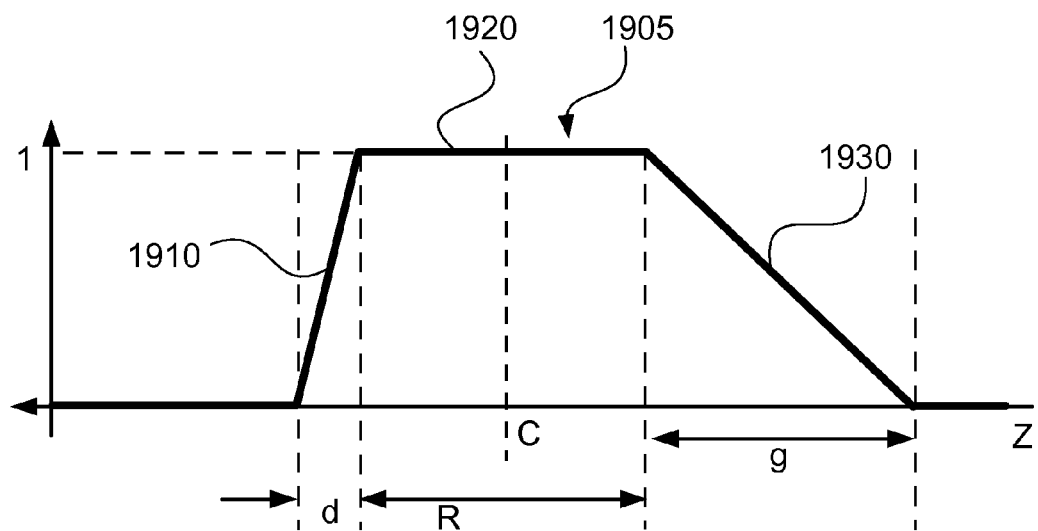
FIGS. 19A, 19B and 19C show examples of different score calculations for curve selection.
Figure 19B:
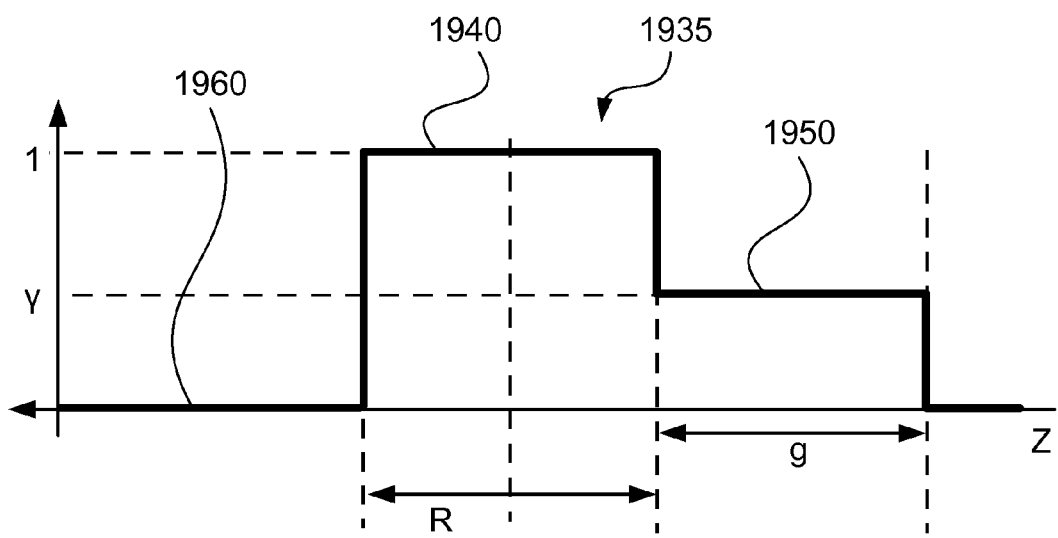
Figure 19C:
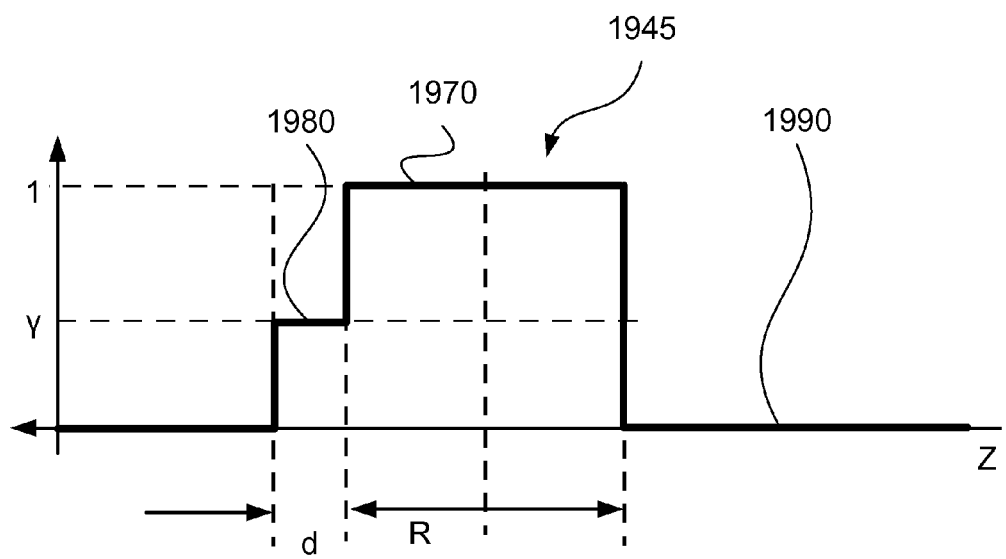

Examples of the asymmetric scoring function used in step 1840 are shown in FIGS. 19A, 19B and 19C. FIG. 19A shows one example of the asymmetric scoring function 1905 where a piecewise linear function models weights for the depolarizing tissue. The piecewise linear function 1905 in FIG. 19A comprises three (3) linear segments. A left segment 1910 models an arrangement of the small depolarising particles above the assumed healthy RPE layer. A centre segment 1920 models the healthy RPE layer, and a right segment 1930 models an arrangement of the depolarising tissues in the choroid below the RPE. The shape of the linear functions in the segments 1910, 1920 and 1930 are determined using prior knowledge of the eye structure. The slope of the left segment 1910 is determined by a heuristic distance d representing the average offset of a depolarising particle above the healthy RPE layer. For example, for a PS-OCT B-scan with a resolution of 3 microns per pixel, the value of the distance d can be set to 15 microns. The width R of the centre segment 1920 is determined by the average RPE thickness estimated statistically by averaging across a group of patients. For example, for a PS-OCT B-scan with a resolution of 3 microns per pixel, the value of R can be set to 75 microns. The slope of the right segment 1930 is determined by the penetration depth g of the light in choroid. For example, for a PS-OCT B-scan with a resolution of 3 microns per pixel, the value of the GA penetration g can be set to 450 microns. The location C in FIG. 19A marks the Z coordinate of the smooth curve fitted in step 730 for a particular X location.

The score determined in step 1840 is calculated using the asymmetric function 1905 in FIG. 19A, where each test point located in the Z coordinate range marked by the centre segment 1920 is weighted by 1. That is, each test point is weighted by a value that depends upon the distance Z from the smooth curve to the test point. This weighting is zero when the distance to the smooth curve is below $Z=-R/2-d$ or above $Z=R/2+g$. The weighting further increases linearly from 0 at $Z=-R/2-d$ to 1 at $Z=-R/2$, as shown by the segment 1910. The weighting is one when the magnitude of the distance to the smooth curve is less than R/2, as shown by the segment 1920. The weighting further decreases linearly from 1 at $Z=R/2$ to 0 at $$Z = \frac{R}{2} + g,$$

as shown by the segment 1930, where each test point located in the Z coordinate range marked by the segment 1930 is weighted by the linear function illustrated by the segment 1930. Any test point outside of the range marked by the three segments 1910, 1920 and 1930 is weighted by 0. The test points used here are the test points defined previously with reference to Equation (7). The score for a smooth curve fitted in step 730 in FIG. 18 is the sum of all the weights. This score reflects the two important factors in the modelling of the depolarizing data. Firstly, the majority of the data points are indeed RPE tissues evenly distributed around the healthy RPE location. In addition a large number, but not a majority, of data points are from the depolarizing tissues in the choroid and distributed mainly under the healthy RPE location.

The piecewise linear function 1905 shown in FIG. 19A can be modified to used other piecewise smooth functions. For example, the linear segment 1910 can be replaced by any increasing function that goes from 0 to T within a range of d pixels. Similarly, the linear 1930 can be modified to be any decreasing function that goes from T to 0 within a range of approximately g pixels. The centre segment 1920 in FIG. 19A can also be replaced by any number of functions that are asymmetric around the smooth RPE location, $z=C(x)$.

A more simplified approach to asymmetric scoring is illustrated in FIG. 19B, in the form of an asymmetric scoring function 1935. With the function 1935, data locations in the range marked by a segment 1940 are weighted by 1 and data points in the range marked by a segment 1950 are weighted by $\gamma$, where $\gamma$ is a number between 0 and 1. For example, $\gamma=0.4$ can be used. Accordingly, regions above the estimated RPE attract no weight (segment 1960), whereas the other regions attract fixed weights of either 1 (segment 1940) or $\gamma$ (segment 1950). Such simplifies image processing and therefore reduces processing time.

Once each of the smooth curves fitted in step 730 in FIG. 18 is associated with a score, the curve with the highest score is chosen as the candidate for healthy RPE location. Similar to step 760, step 1850 identifies inliers based on the candidate healthy RPE location and fits a final smoothing curve, such as a cubic spline, to the inliers. Using FIGS. 19A and 19B for illustration, the regions marked by the respective segments 1920 and 1940 are used for identifying inliers. That is, data points within R/2 distance from the fitted smooth curve from step 730 are used for fitting the final smoothing cubic spline. This final smooth curve will be the estimated healthy RPE curve used later in the process in FIG. 5.

FIG. 19C shows another asymmetric scoring function 1945, formed of segments 1970, 1980 and 1990.

Figure 21A:
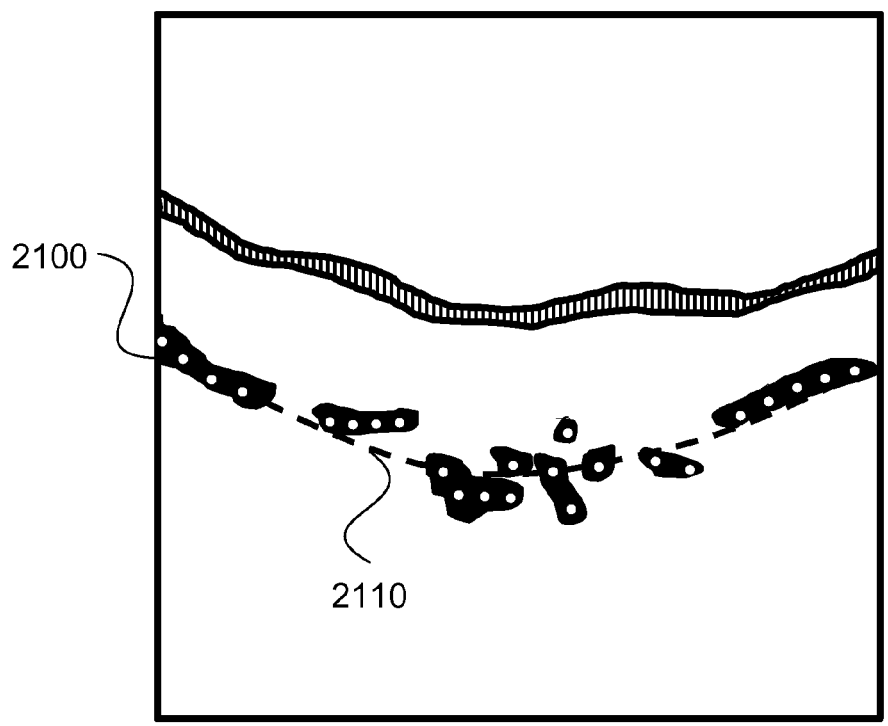
FIGS. 21A and 21B show schematic results from using the described arrangements.

The functions 1905, 1935 and 1945 may each be considered as disease models, or to represent disease related arrangements (or models) of the depolarising regions, in that each can be used, adapted or modified to result in different processing of images to permit the practitioner to better discriminate between different physiological conditions and disease types. For example, with reference to FIGS. 19A, 19B and 19C, the functions 1905 and 1935 may provide for better discrimination of one condition, such as geographic atrophy, while the function 1945, where regions below the estimated RPE attract no weight (segment 1990) and the other regions attract fixed weights of either 1 (segment 1970) or γ (segment 1980), may be used to provide for better discrimination of another condition, such as drusen and other sub-retinal distortions. FIG. 21A shows results of the methods of estimating a healthy RPE location without considering pathology (or disease) related distribution. Shown in FIG. 21A are a number of low DOPU CC regions 2100 with candidate points (white dots) and a smooth curve 2110 (dashed) fitted to some of the selected candidate points, representing corresponding depolarising CC regions. The smooth curve represents the estimated healthy RPE location. In this example without asymmetric distribution the curve will tend to go through tissue that has been segmented below the RPE layer.

Figure 21B:
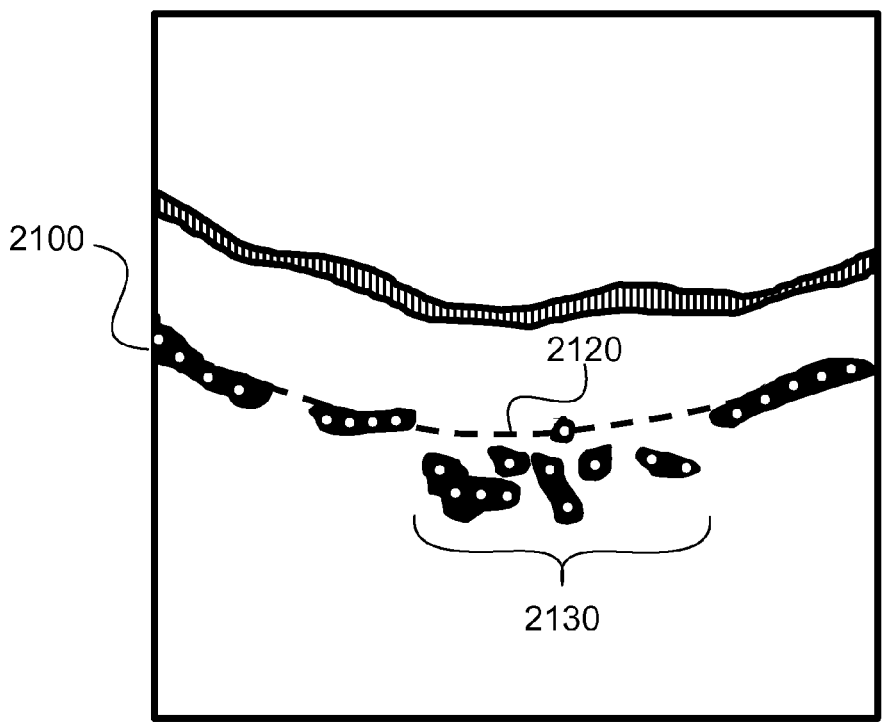

FIG. 21B shows results of the presently disclosed methods using asymmetric pathology related distribution, for the same input image data set of FIG. 21A and depolarizing regions 2100 and where corresponding graphical features are similarly represented. This image shows that with asymmetric distribution, the estimated RPE curve 2120 is moved upwards and, in this example, better agrees with the true healthy RPE curve and intersects the remaining RPE tissue. In addition, unlike FIG. 21A the curve does not pass through the tissue in the choroid that is visible due to the region of geographic atrophy 2130.

Third Implementation

In this implementation, the steps in FIG. 5 are implemented to calculate RPE thickness in a 3D PS-OCT data set, in a manner similar to the first implementation, except that the healthy RPE location estimation step 520 is implemented differently.

Figure 22:
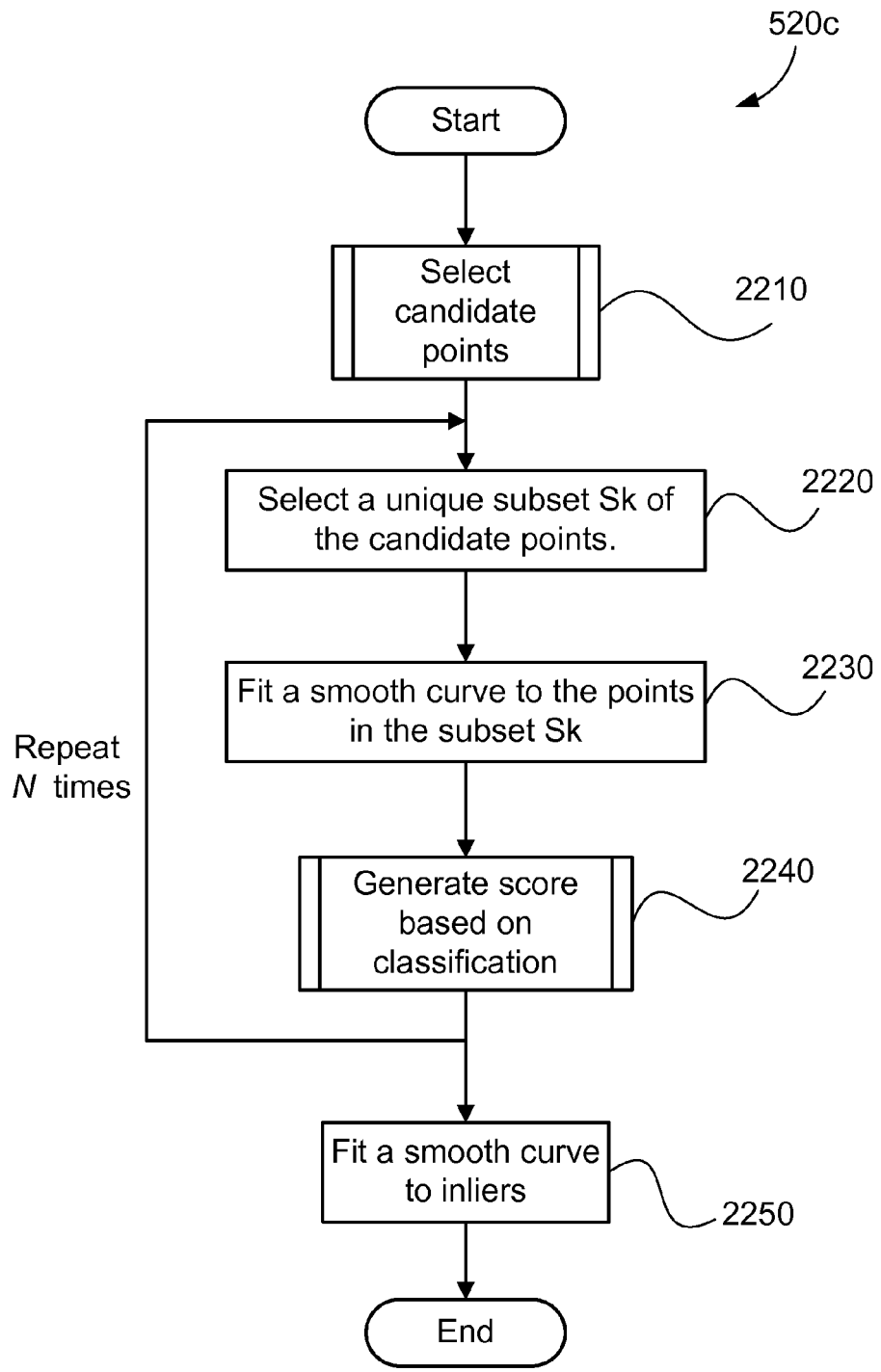
FIG. 22 is a flow diagram explaining the healthy RPE estimation step of FIG. 5 in another implementation.

FIG. 22 shows a preferred process 520c applicable to the third implementation of the process of estimating healthy RPE location 520. First, a candidate point selection process 2210 is used to select the candidate points, and which corresponds to that as described above in step 710 of FIG. 7. A unique subset of these candidate points is then chosen in step 2220, as was done in step 720 of FIG. 7. A smooth curve fitting process 2230 is then used to fit a candidate smooth curve to the chosen subset, corresponding to what was done in step 730 of FIG. 7.

In order to generate the score for each curve fitting, a process 2240 is applied so that information, calculated as features at or around data points, in addition to point locations, can be incorporated. In step 2250, the scores of the fitted curves are examined to choose the best smooth curve, which is then used to identify inliers that are used to fit a final smooth curve, in a similar fashion as was done in step 760. The final smooth curve forms the estimate of the smooth RPE location, concluding the process 520c.

In process 2240, the score for each of the fitted smooth curves is calculated using a training-classification method. That is, using the candidate points selected in step 2210 from some training B-scans and selected features of these example candidate points, a classifier is trained to classify the candidate points selected in step 2210 from an arbitrary input B-scan. Input B-scans are not restricted to those used in training, although a good set of training B-scans should be representative of expected input B-scans. The selected features can be certain properties of these candidate points, for example, the values in the intensity image at or around the location of the candidate points. The classification results and the associated confidence score can be used to evaluate how well each of the fitted smooth curves estimates the healthy RPE location.

The classifier used in the process 2240 can be any method that puts a label such as 'RPE' or 'non-RPE' on a candidate point, or provides a score for the point which can be used to classify the point as RPE or non-RPE. In a preferred implementation of process 520c, a positive score represents an RPE classification and a negative score represents non-RPE classification, with the absolute value of the score representing the confidence of the classification. The output of a classifier that only provides labels can be trivially mapped to a score by interpreting label 'RPE' as score 1 and label 'non-RPE' as score −1. The classifier can be a linear classifier or a non-linear classifier. In this disclosure, a logistic regression classifier, being a type of linear classifier, is used for descriptive purposes and without loss of generality. Logistic regression measures the linear relationship between the features and the tissue label of a data point by estimating probabilities using the logistic function. Training a logistic regression classifier generates a group of coefficients, one coefficient for each feature, that are used to describe the above mentioned linear relationship.

Figure 24:
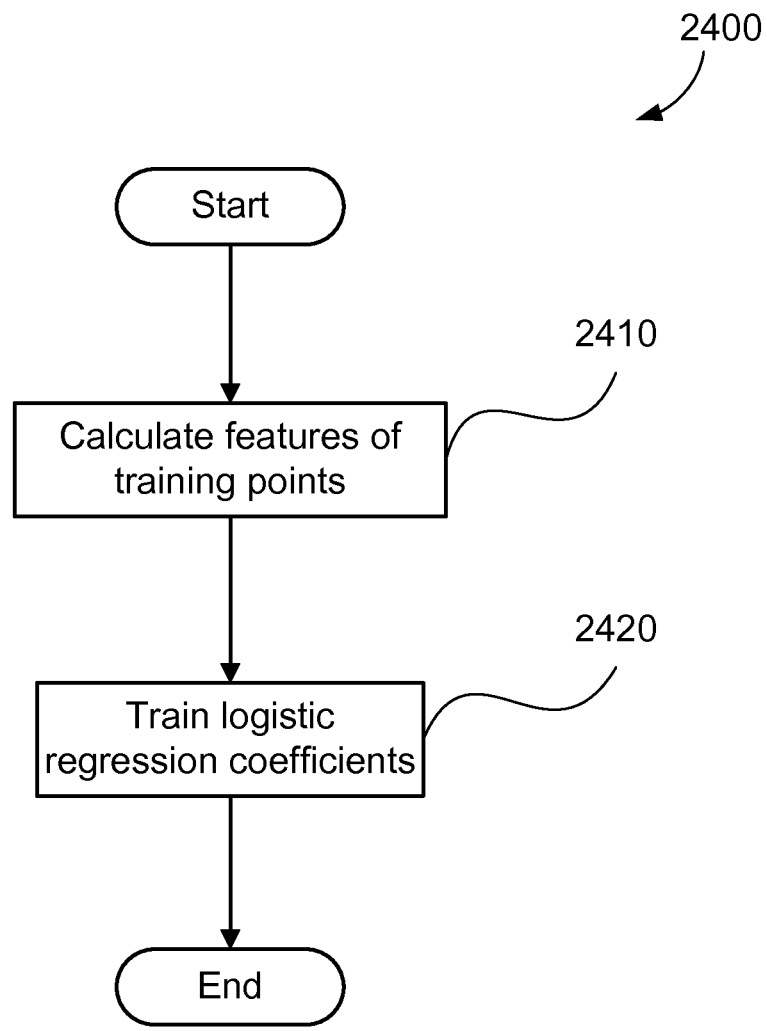
FIG. 24 is flowchart of the training process that generates the logistic regression coefficients for the process of FIG. 22.

FIG. 24 describes a preferred training process 2400 that generates the logistic regression coefficients. The training process 2400 is performed on a group of training B-scans where ground truth labels of 'RPE' and 'non-RPE' are available. The ground truth labels are typically set manually by expert readers of PS-OCT or OCT B-scans. Once the logistic regression coefficients are generated, they can be used to describe a linear relationship between the label and a group of features. The features used in this training-classification method will be discussed in detail later with reference to FIG. 25.

In FIG. 24, example candidate points are selected as training points in order to generate logistic regression coefficients. Typically, these training points are a randomly selected subset of the candidate points as selected in step 2210. As explained previously, these training points are selected from a group of training B-scan where ground truth labels are available. Step 2410 of the process 2400 calculates the features of each randomly selected training point. Step 2420 then trains logistic regression coefficients using the calculated features and the ground truth. In step 2420, the logistic regression coefficients are calculated through the maximization of a log-likelihood function, equation (8):

$$J(\theta) = \frac{1}{m}\sum_{i=1}^{m}[c_i\log(h(F_i)) + (1-c_i)\log(1-h(F_i))] + \frac{\lambda}{2m}\sum_{j=1}^{n}\theta_j^2 \quad (8)$$

where $$h(F_i) = 1/\left(1 + e^{-\theta^T F_i}\right) \quad (9)$$

m is the number of training points,
n is the number of features, and
λ∈R is the regularization parameter.

In Equations (8) and (9):

$F_i$ is the (n+1)-by-1 features vector for the ith training point, where the first element of $F_1$ is always 1;

θ is an (n+1)-by-1 vector representing the logistic regression coefficients, where $\theta_0$ is the 'intercept' corresponding to the first element of $F_i$ (i.e. the coefficient $\theta_0$ multiplied by the constant first feature of $F_i$ provides a constant offset in the linear combination of coefficients and features); and $c_i$ is the ground truth label of each training point, where a value of 0 indicates non-RPE and 1 indicates RPE tissue type.

For example, for a group of 100 training points, if 15 features are used, i.e., m=100, n=15, each of the 100 feature vectors $F_i$ will be (15+1)-by-1 with the first element being always 1. In the training process 2420, given the ground truth label $c_i$ and the feature vector $F_i$ for each training point, an optimal coefficient vector θ, maximizing equation (8), can be found using optimization methods such as gradient descent or normal equations.

It should be noted that the training process 2400 described in FIG. 24 is typically performed before the healthy RPE location estimation step 520c. The classification process 2240 uses pre-calculated logistic regression coefficients to classify the candidate points selected in 2210.

Figure 23:
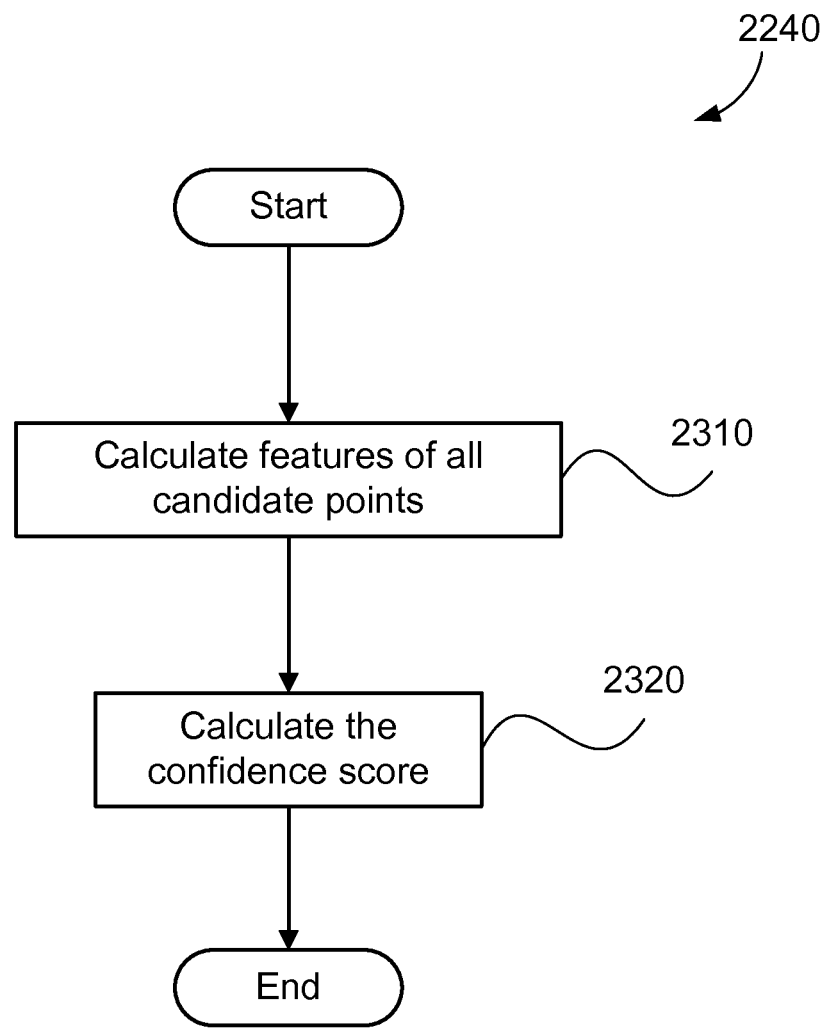
FIG. 23 shows detail of the score generation of the process of FIG. 22.

FIG. 23 is a flowchart of a preferred classification process 2240 that generates the score for a fitted smooth curve. In step 2310 the processor 2005 calculates a group of features for each of the candidate points from the input B-scan. Examples of calculated features are given in detail later with reference to FIG. 25. In one implementation of process 520c, the point features to be calculated at step 2310 are independent of the curve fitted in step 2230, so they may be pre-calculated after selecting the candidate points at 2210, instead of calculating the features at step 2310. In step 2320, the pre-calculated logistic regression coefficients from process 2400 are combined by the processor 2005 with the calculated features to calculate a confidence score for each candidate point. The confidence scores of some candidate points are then accumulated to generate one score for the current curve.

In the preferred implementation of process 520c, the confidence score for each fitted smooth curve can be generated by accumulating the inner product of the feature vector $F_i$ and the coefficient vector θ across all candidate points that belong to an inlier set R:

$$f = \sum_{i \in R} \theta^T F_i \qquad (10)$$

The inlier set R can be selected using fixed distances above and below the fitted smooth curve, as illustrated by 1670 and 1680 in FIG. 16.

Alternatively, the inlier set R can be selected based on the classification results from the logistic regression classifier. For example, when the features used in step 2410 include the distance from a training point to a fitted smooth curve, the logistic regression classification which puts a label of 'RPE' or 'non-RPE' on a candidate point in step 2210 will tend to classify a candidate point as 'RPE' if it is close to the current fitted smooth curve and 'non-RPE' if it is far away from the current fitted smooth curve. Therefore, the logistic regression classification acts as an inlier selection. That is, the candidate points classified by the logistic regression classifier as 'RPE' can be considered inliers. Because the binary logistic regression classifier classifies a candidate point as 'RPE' if its confidence score $\theta^T F_i > 0$, the inlier set R can be simply the set of candidate points with positive classification scores $\theta^T F_i$. That is, $$f = \Sigma_{\theta^T F_i > 0} \theta^T F_i.$$

In step 2250, the fitted smooth curve with the highest confidence score will then be chosen as the best curve and used to define inliers.

Selection of training and classification features is typically based on observation or using certain tools such as L1-norm regularized logistic regression. Features used in the training and classification process desirably should be strongly correlated with the tissue types. In other words, a collection of features should be able to distinguish between the RPE tissue and the non-RPE tissue. Example features include, but are not limited to: the average DOPU and the average intensity values for the connected component that the candidate point belongs to, the size of the connected component in pixels, the ratio of the connected component size to perimeter length, values in the DOPU and the intensity image at or around the candidate point location, and the slopes of lines fitted above and below the candidate point in the intensity A-scan.

Figure 25:
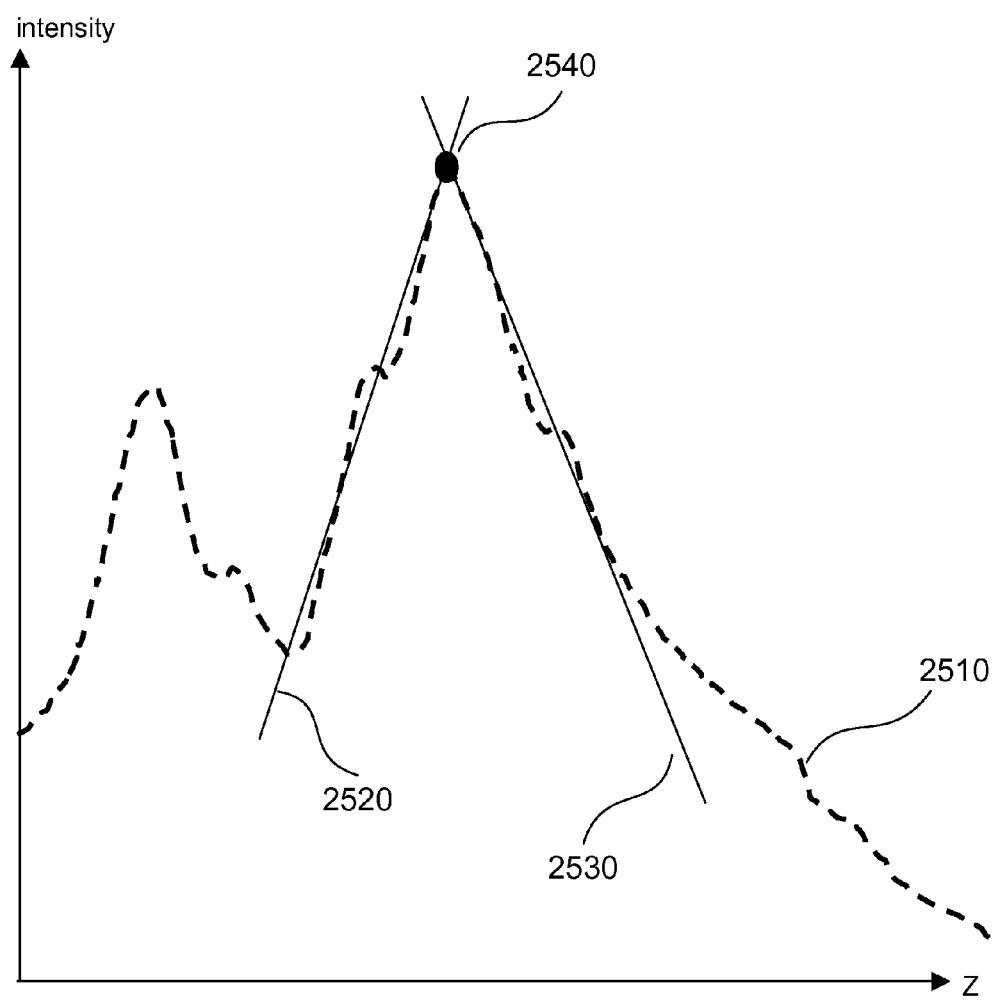
FIG. 25 illustrates the slope above and below a candidate point in the intensity A-scan.

FIG. 25 illustrates the slope above and below a candidate point in the intensity A-scan. In FIG. 25, the dashed line 2510 represents the intensity of an A-scan in the z direction. The straight lines 2520 and 2530 are fitted to 2510 just above (smaller z coordinate value) and below (larger z coordinate value) a candidate point 2540. Candidate points sitting close to an intensity peak, as the example shown in FIG. 25, will typically have different values for the slopes of the straight lines 2520 and 2530 than for the above and below slopes for a point sitting far away from a peak. Therefore, this information can be utilized to separate RPE from non-RPE tissues based on where the two tissue types generally fall relative to intensity peaks.

INDUSTRIAL APPLICABILITY

The arrangements described are applicable to the computer and data processing industries, and particularly for the processing of retinal images. Such processing can assist practitioners of diagnosing conditions of the eye.

The foregoing describes only some embodiments of the present invention, and modifications and/or changes can be made thereto without departing from the scope and spirit of the invention, the embodiments being illustrative and not restrictive.

We claim:

1. A computer implemented method for determining a retinal pigment epithelium, the method comprising:
    identifying a plurality of regions by calculating a degree of polarization uniformity value using captured image data of an eye, the captured image data being polarization-sensitive OCT data of the eye;
    fitting, by a processor, a plurality of curves to at least some of the identified regions, each fitted curve defining at least one first depolarising region at a predetermined distance above the fitted curve and at least one second depolarising region at the predetermined distance below the fitted curve;
    for each of the fitted curves, determining, by the processor, a curve score, wherein contribution of a corresponding at least one second depolarizing region is weighted higher than contribution of a corresponding at least one first depolarizing region;
    comparing, by the processor, the determined curve scores;
    selecting, by the processor, one of the fitted curves using a result of the comparing to determine a position of a healthy retinal pigment epithelium (RPE) of the eye;
    generating an en face RPE thickness map using the determined position of the healthy retinal pigment epithelium; and
    evaluating at least one of size and the number of at least one of diseased regions in the en face RPE thickness map.

2. A method according to claim 1, wherein the captured image data comprises at least one B-scan slice of retina, the B-scan slice comprises intensity image data and polarisation data of an area of an eye.

3. A method according to claim 2, further comprising using the intensity image data and polarisation data to produce degree of polarisation uniformity (DOPU) data.

4. A method according to claim 3, wherein the identifying a plurality of regions comprises determining a plurality of connected components of the DOPU data, so that each depolarising region in the DOPU data is described as at least one connected component.

5. A method according to claim 1, wherein depolarising regions below a curve from the plurality of fitted curves are weighted higher than depolarising regions above the curve in determining a curve score.

6. The method according to claim 1, further comprising:
 selecting depolarising regions within a further predetermined distance to the selected fitted curve, wherein the further predetermined distance relates to an expected thickness of the retinal pigment epithelium;
 fitting a smooth RPE curve to the selected depolarising regions;
 classifying depolarising regions of the captured image data as forming at least one of RPE tissues, choroid tissues, and other depolarising particles using the fitted smooth RPE curve.

7. A method according to claim 6, wherein a depolarising region is classified as being part of the RPE if the depolarising region substantially falls within the predetermined distance to the fitted RPE curve.

8. A method according to claim 7, wherein a depolarising region is classified as choroid if the depolarising region is below the fitted RPE curve at a distance exceeding the predetermined distance.

9. A method according to claim 6, wherein a depolarising region is classified as belonging to other depolarising particles if the depolarising region is above the selected fitted curve at a distance exceeding the further predetermined distance.

10. A method according to claim 6, wherein the depolarising regions are classified using corresponding shape descriptors.

11. A method according to claim 1, wherein the captured image data comprises at least one B-scan slice of retina, the B-scan slice comprises intensity image data and polarisation data of an area of an eye, the method further comprising using the intensity image data and polarisation data to produce degree of polarisation uniformity (DOPU) data, wherein the identifying a plurality of regions comprises determining a plurality of connected components of the DOPU data, so that each depolarising region in the DOPU data is described as at least one connected component.

12. The method according to claim 1, wherein the one of the fitted curves is selected by weighting contribution of the at least one second depolarising region higher than contribution of the at least one first depolarising region.

13. A method according to claim 1, wherein the curve score is determined by asymmetrically biasing toward the second plurality of depolarizing regions.

14. A method according to claim 1,
 wherein the curve score associated with the each fitted curve is determined using at least a distance between the each fitted curve and at least some of the identified regions, and wherein a contribution of the identified regions to the curve score is determined by asymmetrically biasing toward the second plurality of depolarizing regions.

15. The method according to claim 1, further comprising:
 selecting a candidate PRE curve using the result of the comparing;
 selecting depolarizing regions within a further predetermined distance to the candidate RPE curve, wherein the further predetermined distance relates to an expected thickness of the RPE curve of the eye; and
 fitting a smooth curve to the selected depolarizing regions to determine the position of the healthy RPE of the eye.

16. The computer implemented method according to claim 1, further comprising:
 classifying depolarizing regions of the captured image data as forming at least one of PRE tissue, choroid tissues, and other depolarizing particles using the position of the healthy retinal pigment epithelium.

17. The computer implemented method according to claim 1, further comprising:
 using the en face RPE thickness map to diagnose advanced stage of age-related macular degeneration (AMD) by evaluating the size and the number of geographic atrophy (GA) regions as the diseased regions in the en face RPE thickness map.

18. A non-transitory computer readable storage medium having a program recorded thereon, the program being executable by computerised apparatus to determine a retinal pigment epithelium, the program comprising:
 code for identifying a plurality of regions by calculating a degree of polarization uniformity value using captured image data of an eye, the captured image data being polarization-sensitive OCT data of the eye;
 code for fitting a plurality of curves to at least some of the identified regions, each fitted curve defining at least one first depolarising region at a predetermined distance above the fitted curve and at least one second depolarising region at the predetermined distance below the fitted curve;
 for each of the fitted curves, code for determining a curve score, wherein contribution of a corresponding at least one second depolarizing region is weighted higher than contribution of a corresponding at least one first depolarizing region;
 code for comparing the determined curve scores;
 code for selecting one of fitted curves using a result of comparing to determine a position of a healthy retinal pigment epithelium (RPE) of the eye;
 code for generating an en face RPE thickness map using the determined position of the healthy retinal pigment epithelium; and
 code for evaluating at least one of size and the number of at least one of diseased regions in the en face RPE thickness map.

19. The non-transitory computer readable storage medium according to claim 18, the program further comprising:
 code for classifying depolarizing regions of the captured image data as forming at least one of RPE tissues, choroid tissues, and other depolarizing particles using the position of the healthy retinal pigment epithelium.

20. The non-transitory computer readable storage medium according to claim 18, the program further comprising:
 code for using the en face RPE thickness map to diagnose advanced stage of age-related macular degeneration (AMD) by evaluating the size and the number of geographic atrophy (GA) regions as the diseased regions in the en face RPE thickness map.

21. A system for determining retinal pigment epithelium (RPE), the system comprising:
- a source of optical coherence tomography (OCT) images representing captured image data of an eye;
- a computer system having a processor coupled to a memory, the memory storing a program for execution by the processor to determine the RPE, the program comprising:
- code for identifying a plurality of regions by calculating a degree of polarization uniformity value using the captured image data of the eye, the captured image data being polarization-sensitive OCT data of the eye;
- code for one of:
- (A) (A)(i) fitting, by the processor, a curve into at least some of the identified regions;
- (A)(ii) determining, by the processor, a curve score associated with the fitted curve, wherein a contribution of regions below the fitted curve is weighted higher than contribution of corresponding regions above the fitted curve;
- (A)(iii) repeating steps (A)(i) and (A)(ii) at least once;
- (A)(iv) comparing, by the processor, the determined scores;
- (A)(v) selecting, by the processor, one of the fitted curves, using a result of the comparing to determine a position of a healthy retinal pigment epithelium (RPE) of the eye;
- (B) (B)(i) fitting, by the processor, a plurality of curves to at least some of the identified regions, each fitted curve defining at least one first depolarising region at a predetermined distance above the fitted curve and at least one second depolarising region at the predetermined distance below the fitted curve;
- (B)(ii) for each of the fitted curves, determining, by the processor, a curve score, wherein the contribution of a corresponding at least one second depolarizing region is weighted higher than contribution of a corresponding at least one first depolarizing region;
- (B)(iii) comparing, by the processor, the determined score curve; and
- (B)(iv) selecting, by the processor, one of the fitted curves using a result of the comparing to determine a position of a healthy retinal pigment epithelium (RPE) of the eye;
- code for generating an en face RPE thickness map using the determined position of the healthy retinal pigment epithelium; and
- code for evaluating at least one of size and the number of at least one of diseased regions in the en face RPE thickness map.

22. The system according to claim 19, wherein:
the steps (A) (A)(i) fitting, by the processor, a curve into at least some of the identified regions;
- (A)(ii) determining, by the processor, a curve score associated with the fitted curve, wherein contribution of regions below the fitted curve is weighted higher than contribution of corresponding regions above the fitted curve;
- (A)(iii) repeating steps (A)(i) and (A)(ii) at least once;
- (A)(iv) comparing, by the processor, the determined curve scores; and
- (A)(v) selecting, by the processor, one of the fitted curves, using a result of the comparing to determine a position of a healthy retinal pigment epithelium (RPE) of the eye; further comprise:
- (A)(vi) classifying depolarizing regions of the captured image data as forming at least one of RPE tissues, choroid tissues, and other depolarizing particles using the position of the healthy retinal pigment epithelium (RPE); and the steps (B) (B)(i) fitting, by the processor, a plurality of curves to at least some of the identified regions, each fitted curve defining at least one first depolarising region at a predetermined distance above the fitted curve and at least one second depolarising region at the predetermined distance below the fitted curve;
- (B)(ii) for each of the fitted curves, determining, by the processor, a curve score, wherein the contribution of a corresponding at least one second depolarizing region is weighted higher than contribution of a corresponding at least one first depolarizing region;
- (B)(iii) comparing, by the processor, the determined curve scores; and
- (B)(iv) selecting, by the processor, one of the fitted curves using a result of the comparing to determine a position of a healthy retinal pigment epithelium (RPE) of the eye; further comprise:
- (B)(v) classifying depolarizing regions of the captured image data as forming at least one of RPE tissues, choroid tissues, and other depolarizing particles using the position of the healthy retinal pigment epithelium.

23. The system according to claim 19, the program further comprising:
- code for using the en face RPE thickness map to diagnose advanced stage of age-related macular degeneration (AMD) by evaluating the size and the number of geographic atrophy (GA) regions as the diseased regions in the en face RPE thickness map.

* * * * *